(12) United States Patent
Hershkovich et al.

(10) Patent No.: US 12,397,167 B2
(45) Date of Patent: Aug. 26, 2025

(54) COMPOSITIONS AND METHODS OF ALTERING THE ELECTRIC IMPEDANCE TO AN ALTERNATING ELECTRIC FIELD

(71) Applicant: NOVOCURE GMBH, Root (CH)

(72) Inventors: Hadas Hershkovich, Haifa (IL); Tali Voloshin-Sela, Haifa (IL); Ze'ev Bomzon, Haifa (IL)

(73) Assignee: NOVOCURE GMBH, Root (CH)

( * ) Notice: Subject to any disclaimer, the term of this patent is extended or adjusted under 35 U.S.C. 154(b) by 0 days.

(21) Appl. No.: 18/526,789

(22) Filed: Dec. 1, 2023

(65) Prior Publication Data

US 2024/0207629 A1  Jun. 27, 2024

Related U.S. Application Data

(63) Continuation of application No. 17/106,531, filed on Nov. 30, 2020, now Pat. No. 11,833,362.
(Continued)

(51) Int. Cl.
*A61N 1/36* (2006.01)
*A61N 1/32* (2006.01)
(Continued)

(52) U.S. Cl.
CPC ............ *A61N 1/406* (2013.01); *A61N 1/327* (2013.01); *A61N 1/36002* (2017.08); *G06T 7/0012* (2013.01); *G06T 2207/30096* (2013.01)

(58) Field of Classification Search
CPC .... A61N 1/406; A61N 1/327; A61N 1/36002; A61N 1/325; A61N 1/40; G06T 7/0012;
(Continued)

(56) References Cited

U.S. PATENT DOCUMENTS 8,892,200 B2 * 11/2014 Wagner ............... A61N 1/36025
                                                    607/45
2008/0241262 A1 * 10/2008 Lee ............................ B22F 1/17
                                                    428/407
(Continued)

FOREIGN PATENT DOCUMENTS

MX  2017 010 319 A      2/2019
WO  WO-2019100016 A1 *  5/2019 ............. A61K 38/08

OTHER PUBLICATIONS

International Search Report and Written Opinion dated Mar. 9, 2021 for PCT/IB2020/001002, filed Nov. 30, 2020.
(Continued)

*Primary Examiner* — Ankit D Tejani
*Assistant Examiner* — Joshua Brendon Solomon
(74) *Attorney, Agent, or Firm* — BALLARD SPAHR LLP

(57) ABSTRACT

Disclosed are methods of altering the electric impedance to an alternating electric field in a target site of a subject, comprising introducing a nanoparticle to a target site in the subject; and applying an alternating electric field to the target site of the subject, wherein the electric impedance in the target site of the subject to the alternating current is altered. Disclosed are methods for improving transport of a nanoparticle across a cell membrane of a cell, the method comprising applying an alternating electric field to the cell for a period of time, wherein application of the alternating electric field increases permeability of the cell membrane; and introducing the nanoparticle to the cell, wherein the increased permeability of the cell membrane enables the nanoparticle to cross the cell membrane. Disclosed are methods of imaging a cancer cell, the method comprising applying a first alternating electric field at a first frequency to the cancer cell for a first period of time, wherein application of the first alternating electric field at the first frequency to the cancer cell for the first period of time increases
(Continued)

permeability of cell membranes of the cancer cell; introducing a nanoparticle to the cancer cell, wherein the increased permeability of the cell membranes enables the nanoparticle to cross the cancer cell membrane; and imaging the cancer cell.

13 Claims, 9 Drawing Sheets

Related U.S. Application Data

(60) Provisional application No. 62/946,798, filed on Dec. 11, 2019.

(51) Int. Cl.
*A61N 1/40* (2006.01)
*G06T 7/00* (2017.01)

(58) Field of Classification Search
CPC . G06T 2207/30096; A61K 9/51; A61P 35/00; B82Y 5/00
See application file for complete search history.

(56) References Cited

U.S. PATENT DOCUMENTS

| | | | | |
|---|---|---|---|---|
| 2010/0261994 | A1* | 10/2010 | Davalos | A61B 18/1477 600/407 |
| 2013/0261683 | A1* | 10/2013 | Soikum | A61P 35/00 435/173.7 |
| 2014/0121728 | A1* | 5/2014 | Dhillon | A61N 1/0502 607/96 |
| 2019/0117973 | A1* | 4/2019 | Schmidt | A61N 1/36031 |
| 2020/0368525 | A1* | 11/2020 | Maag | A61N 1/0412 |

OTHER PUBLICATIONS

Agarwal, R. et al., Mammalian cells preferentially internalize hydrogel nanodiscs over nanorods and use shape-specific uptake mechanisms, Proc. Natl. Acad. Sci. U S A 110, 17247-17252 (2013).
Armitasari, L. et al., Effect of Polyethylene Glycol (PEG-4000) on Dielectric Properties of Mn0.5Zn0.5Fe2O4 Nanoparticles, 2018 *IOP Conf. Ser.: Mater. Sci. Eng.* 367 012035.
Ballo, M., et al., P01.113 Increasing TTFields dose to the tumor bed improves overall survival in newly diagnosed glioblastoma patients, *Neuro-Oncology*, vol. 20, Issue suppl_3, Sep. 19, 2018, pp. iii257, https://doi.org/10.1093/neuonc/noy139.155.
Branter, J., Basu, S. & Smith, S., Tumour treating fields in a combinational therapeutic approach, Oncotarget 9, 36631-36644 (2018).
Chang, E. et al. Tumor treating fields increases membrane permeability in glioblastoma cells. Cell Death Discov. 4, 113 (2018).
Ciofani, G. et al. Barium titanate nanoparticles: highly cytocompatible dispersions in glycol-chitosan and doxorubicin complexes for cancer therapy. Nanoscale Res. Lett. 5, 1093-1101 (2010).
Ciofani, G. et al. Preparation of stable dispersion of barium titanate nanoparticles: potential applications in biomedicine. Colloids Surf. B Biointerfaces 76, 535-543 (2010).
Ciofani, G. et al. Effects of barium titanate nanoparticles on proliferation and differentiation of rat mesenchymal stem cells. Colloids Surf. B Biointerfaces 102, 312-320 (2013).
Dempsey, C., Coating barium titanate nanoparticles with polyethylenimine improves cellular uptake and allows for coupled imaging and gene delivery, Colloids Surf. B Biointerfaces 112, 108-112 (2013).
Fabian, D. et al., Treatment of glioblastoma (GBM) with the addition of tumor-treating fields (TTF): a review, Cancers (Basel) 11, 174 (2019).

Genchi, G. G., et al., Barium titanate nanoparticles: promising multitasking vectors in nanomedicine, Nanotechnology 27, 232001 (2016).
Giladi, M., et al., Mitotic disruption and reduced clonogenicity of pancreatic cancer cells in vitro and in vivo by tumor treating fields. Pancreatology 14, 54-63 (2014).
Giladi, M., et al., Mitotic spindle disruption by alternating electric fields leads to improper chromosome segregation and mitotic catastrophe in cancer cells. Sci. Rep. 5, 18046 (2015).
Giladi, M. et al. Tumor treating fields (TTFields) delay DNA damage repair following radiation treatment of glioma cells. Radiat. Oncol. 12, 206 (2017).
Hershkovich, HS, et al., First steps to creating a platform for high throughput simulation of TTFields, Conf. Proc. IEEE Eng Med Biol Soc. Aug. 2016; 2016 :2357-2360. doi: 10.1109/EMBC.2016. 7591203.
Jamal, A., et al., Characterization of barium titanate prepared via mixed oxide sintering route, J. Pak. Mater. Soc. 2, 91-95 (2008).
Jamilpanah, P., et al., Thermal conductivity, viscosity, and electrical conductivity of iron oxide with a cloud fractal structure, Heat Mass Transfer (2017) 53: 1343. https://doi.org/10.1007/s00231-016-1891-5.
Jiang, B., et al., Barium titanate at the nanoscale: controlled synthesis and dielectric and ferroelectric properties, Chem. Soc. Rev. 48, 1194-1228 (2019).
Jo, Y., et al., Functional biological activity of sorafenib as a tumor-treating field sensitizer for glioblastoma therapy, Int. J. Mol. Sci. 19, 3684 (2018).
Karanam, N. K., et al., Tumor-treating fields elicit a conditional vulnerability to ionizing radiation via the downregulation of BRCA1 signaling and reduced DNA double-strand break repair capacity in non-small cell lung cancer cell lines, Cell Death. Dis. 8, e2711 (2017).
Kessler, A. F., et al., Effects of tumor treating fields (TTFields) on glioblastoma cells are augmented by mitotic checkpoint inhibition, Cell Death Discov. 4, 12 (2018).
Kim, J.S., et al., CIP2A modulates cell-cycle progression in human cancer cells by regulating the stability and activity of Plk1, Cancer Res. 73, 6667-6678 (2013).
Kim, E. H., et al., Biological effect of an alternating electric field on cell proliferation and synergistic antimitotic effect in combination with ionizing radiation, Oncotarget 7, 62267-62279 (2016).
Kirson, E. D., et al., Disruption of cancer cell replication by alternating electric fields, Cancer Res. 64, 3288-3295 (2004).
Kirson, E. D., et al., (2007), Alternating electric fields arrest cell proliferation in animal tumor models and human brain tumors, Proceedings of the National Academy of Sciences of the United States of America, 104(24), 10152-7.
Kirson, E. D., et al., Chemotherapeutic treatment efficacy and sensitivity are increased by adjuvant alternating electric fields (TTFields), BMC Med. Phys. 9, 1 (2009).
Liu R., et al., Nanoparticle-enhanced electrical impedance detection and its potential significance in image tomography, Int J Nanomedicine. 2013; 8:33-8. doi: 10.2147/IJN.S37275. Epub Jan. 3, 2013.
Marino, A. et al. Piezoelectric barium titanate nanostimulators for the treatment of glioblastoma multiforme. J. Colloid Interface Sci. 538, 449-461 (2019).
Mehta, M., et al., Critical review of the addition of tumor treating fields (TTFields) to the existing standard of care for newly diagnosed glioblastoma patients, Crit. Rev. Oncol. Hematol. 111, 60-65 (2017).
Mun, E. J., et al., Tumor-treating fields: a fourth modality in cancer treatment, Clin. Cancer Res. 24, 266-275 (2018).
Ostovari, M., et al., The Effect of Gold Nanoparticles on Electrical Impedance of Tissue on Low Frequency Ranges, J Biomed Phys Eng. Sep. 1, 2018;8(3):241-250. eCollection Sep. 2018.
Sadat, Sams M. A., et al., A., Effects of size and surface charge of polymeric nanoparticles on in vitro and in vivo applications, Journal of Biomaterials and Nanobiotechnology 7, 91-108 (2016).
Singh, R. & Ulrich, R. K., High and low dielectric constant materials, Interface 8, 26-30 (1999).
Sneider, A., et al., Remotely triggered nano-theranostics for cancer applications, Nanotheranostics 1, 1-22 (2017).

(56) References Cited

OTHER PUBLICATIONS

Stupp, R., et al., NovoTTF-100A versus physician's choice chemotherapy in recurrent glioblastoma: a randomised phase III trial of a novel treatment modality, Eur. J. Cancer 48, 2192-2202 (2012).

Stupp, R., et al., Maintenance Therapy With Tumor-Treating Fields Plus Temozolomide vs Temozolomide Alone for Glioblastoma: A Randomized Clinical Trial, JAMA 314, 2535-2543 (2015).

Stupp, R., et al., Effect of tumor-treating fields plus maintenance temozolomide vs maintenance temozolomide alone on survival in patients with glioblastoma: a randomized clinical trial, JAMA 318, 2306-2316 (2017).

Swanson, K. D., et al., An overview of alternating electric fields therapy (novottf therapy) for the treatment of malignant glioma, Curr. Neurol. Neurosci. Rep. 16, 8 (2016).

Toms, S. A., et al., Increased compliance with tumor treating fields therapy is prognostic for improved survival in the treatment of glioblastoma: a subgroup analysis of the EF-14 phase III trial, J. Neurooncol. 141, 467-473 (2019).

Urman, N., et al., P04.57 Creating patient-specific computational head models for the study of tissue-electric field interactions using deformable templates, *Neuro-Oncology*, vol. 20, Issue suppl 3, Sep. 19, 2018, pp. iii292, https://doi.org/10.1093/neuonc/noy139.291.

Voloshin, T. et al. Alternating electric fields (TTFields) in combination with paclitaxel are therapeutically effective against ovarian cancer cells in vitro and in vivo. Int. J. Cancer 139, 2850-2858 (2016).

Wenger, C., et al., The electric field distribution in the brain during TTFields therapy and its dependence on tissue dielectric properties and anatomy: a computational study, Phys Med Biol. 2015; 60(18):7339-57.

Yoon, Y. N., et al., MASTL inhibition promotes mitotic catastrophe through PP2A activation to inhibit cancer growth and radioresistance in breast cancer cells, BMC Cancer 18, 716 (2018).

\* cited by examiner

COMPOSITIONS AND METHODS OF ALTERING THE ELECTRIC IMPEDANCE TO AN ALTERNATING ELECTRIC FIELD

CROSS-REFERENCE TO RELATED APPLICATIONS

This application is a continuation of U.S. application Ser. No. 17/106,531, filed Nov. 30, 2020, which claims benefit of U.S. Provisional Application No. 62/946,798 filed Dec. 11, 2019 and is hereby incorporated herein by reference in their entirety.

BACKGROUND

Tumor Treating Fields, or TTFields, are typically low intensity (e.g., 1-3 V/cm) alternating electric fields within the intermediate frequency range (100-300 kHz). TTFs through can deliver alternating electric fields through non-invasive transducer arrays across the anatomical region of a tumor. TTFs have been established as an anti-mitotic cancer treatment modality because they interfere with proper micro-tubule assembly during metaphase and eventually destroy the cells during telophase, cytokinesis, or subsequent interphase. TTFields have been shown to not affect the viability of non-dividing normal cells, nerves, and muscles because of their low intensity. TTField therapy is an approved mono-treatment for recurrent glioblastoma, and an approved combination therapy with chemotherapy for newly diagnosed glioblastoma and unresectable malignant pleural mesothelioma patients. These electric fields are induced non-invasively by transducer arrays (i.e., arrays of electrodes) placed directly on the patient's scalp. TTFields also appear to be beneficial for treating tumors in other parts of the body.

BRIEF SUMMARY

Disclosed are methods of altering the electric impedance to an alternating electric field in a site adjacent to a target site of a subject, comprising introducing a non-conductive nanoparticle to a site adjacent to the target site in the subject; and applying an alternating electric field to the site adjacent to the target site of the subject, wherein the electric impedance in the site of the subject to the alternating current is altered.

Disclosed are methods of altering the electric impedance to an alternating electric field in a target site of a subject, comprising introducing a conductive nanoparticle to a target site in the subject; and applying an alternating electric field to the target site of the subject, wherein the electric impedance in the target site of the subject to the alternating current is altered.

Disclosed are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased.

Disclosed are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased.

Disclosed are methods of altering the electric impedance to an alternating electric field in a target site of a subject, comprising introducing a nanoparticle to a target site in the subject; and applying an alternating electric field to the target site of the subject, wherein the electric impedance in the target site of the subject to the alternating current is altered.

Disclosed are methods of increasing the efficacy of an alternating electric field in a target site of a subject, the method comprising introducing a nanoparticle to a target site in the subject; applying an alternating electric field to the target site of the subject, wherein the efficacy of the alternating electric field in the target site of the subject is increased.

Disclosed are methods of increasing the efficacy of an alternating electric field in a target site of a subject, the method comprising introducing a non-conductive nanoparticle to a non-target site adjacent to the target site in the subject; applying an alternating electric field to the target site of the subject, wherein the efficacy of the alternating electric field in the target site of the subject is increased.

Disclosed are methods for improving transport of a nanoparticle across a cell membrane of a cell, the method comprising applying an alternating electric field to the cell for a period of time, wherein application of the alternating electric field increases permeability of the cell membrane; and introducing the nanoparticle to the cell, wherein the increased permeability of the cell membrane enables the nanoparticle to cross the cell membrane.

Disclosed are methods for reducing the viability of cancer cells, the method comprising: applying a first alternating electric field at a first frequency to the cancer cells for a first period of time, wherein application of the first alternating electric field at the first frequency to the cancer cells for the first period of time increases permeability of cell membranes of the cancer cells; introducing a nanoparticle to the cancer cells, wherein the increased permeability of the cell membranes enables the nanoparticle to cross the cell membranes; and applying a second alternating electric field at a second frequency to the cancer cells for a second period of time, wherein the second frequency is different from the first frequency, and wherein the second alternating electric field at the second frequency reduces viability of the cancer cells.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

(FIG. 1A) Axial slices of an MRI of a patient with GBM, with his gross tumor volume region marked (FIG. 1B) Simulation results of a computerized head model resulted from assigning the conductivity of the enhancing tumor tissue a value 0.24 S/m (FIG. 1C) Simulation results of a computerized head model resulted from assigning the conductivity of the enhancing tumor tissue a value 0.3 S/m (FIG. 1D) Relative difference of simulation results of 0.3 S/m vs. 0.24 S/m.

(FIG. 3A) FE-SEM and (FIG. 3B) TEM images of BTNPs. (FIG. 3C) Sizes and zeta-potential values of FBS coated BTNPs.

(FIG. 4A and FIG. 4B) Cell proliferation, (FIG. 4C and FIG. 4D) representative images from clonogenic assays, and (FIG. 4E and FIG. 4F) colony counting in MCF-7 and BT-549 cells upon BTNP treatment. Data represent mean±standard deviation of three independent experiments; **$P<0.01$, and *$P<0.05$. N.S. not significant.

(FIG. 5A) Cell proliferation following TTFields in MCF-7, MDA-MB-231, and BT-549 cells, (FIG. 5B) Relative number of cells with TTFields or TTFields and BTNPs treatment to MCF-7 cells, and (FIG. 5C) quantification of colonies. Data represent mean±standard deviation of three independent experiments; **$P<0.01$, and *$P<0.05$.

(FIG. 6A and FIG. 6B) Flow cytometry histogram and (FIG. 6C and FIG. 6D) representative images showing cytosolic localization of BTNPs in MCF-7 and BT-549 cells treated with TTFields or TTFields and BTNP. (FIG. 6E) TEM images confirming the cytosolic localization of BTNPs in TTField-treated MCF-7 cells. Data is representative of three independent experiments.

(FIG. 7A) Heatmap with global significance scores and global significance statistics and (FIG. 7B) directed global significance scores for cells treated with TTFields or TTFields and BTNPs.

(FIG. 8A) Gene signatures related to cell cycle pathways grouped in a heatmap and (FIG. 8B) Western blot of MCF-7 cells treated with TTFields or TTFields and BTNP. Data is representative of three independent experiments.

DETAILED DESCRIPTION

Figures 1A, 1B, 1C, 1D:
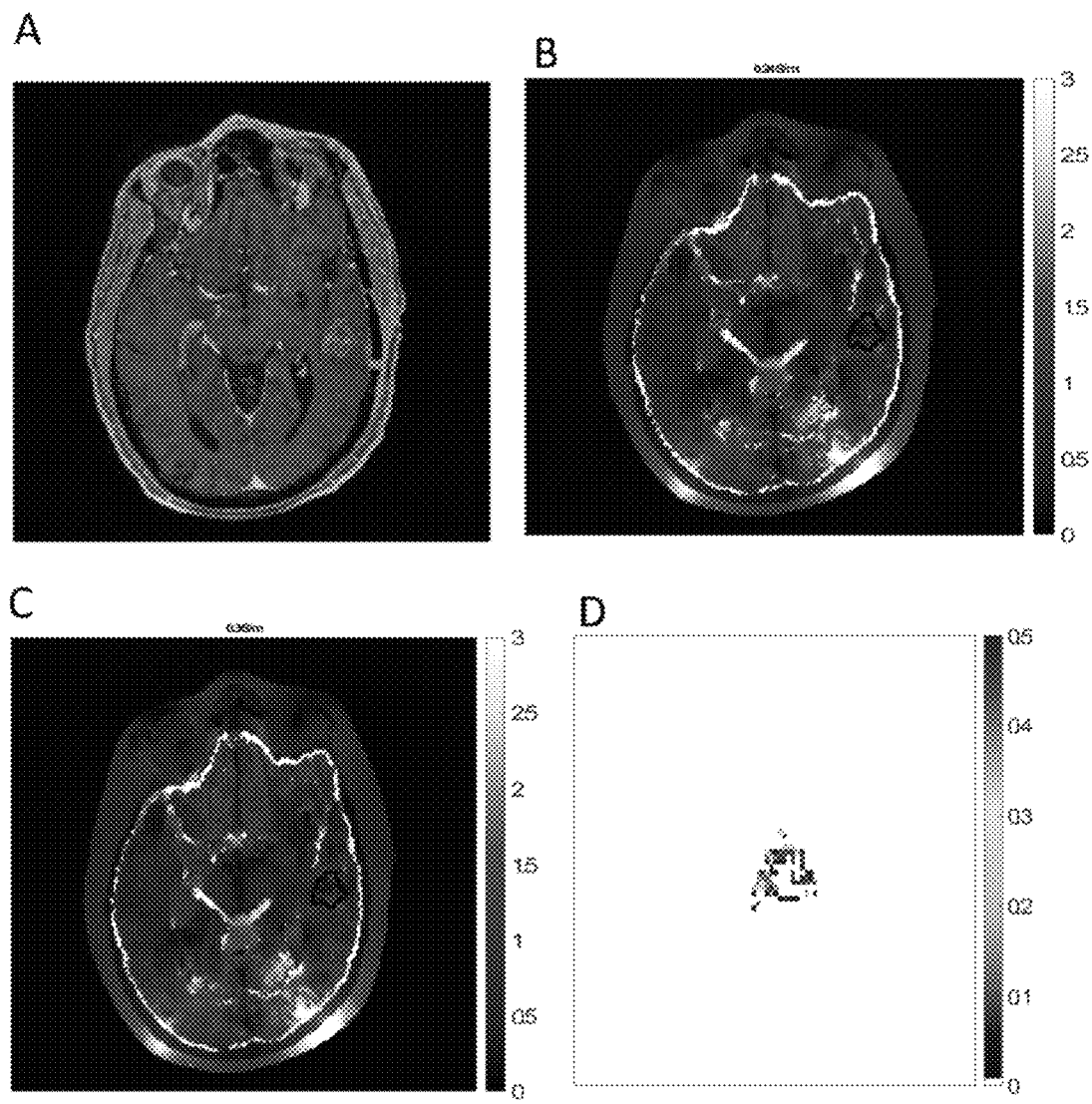
FIG. 1A, FIG. 1B, FIG. 1C, and FIG. 1D show exemplary effects of enhanced tumor conductivity on TTFields intensity.
Figure 2:
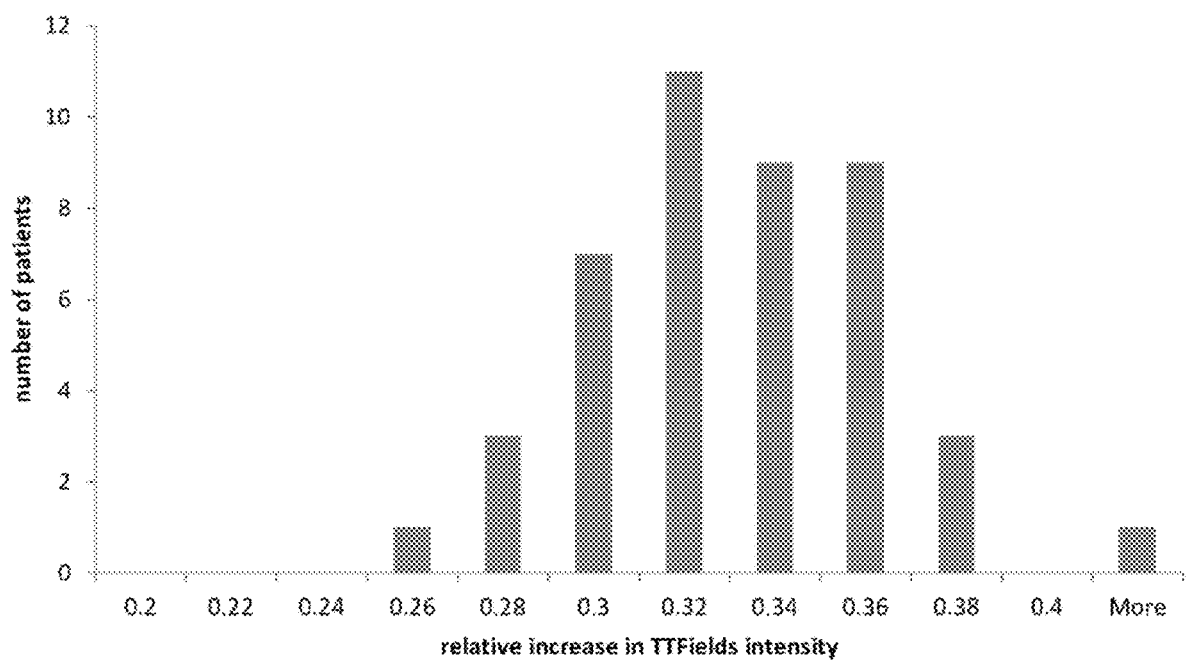
FIG. 2 shows a histogram of average LMiPD in the gross tumor volume of 45 head models of GBM patients treated with TTFields.

The disclosed method and compositions may be understood more readily by reference to the following detailed description of particular embodiments and the Examples included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a nanoparticle" includes a single or a plurality of such nanoparticles, reference to "the nanoparticle" is a reference to one or more nanoparticles and equivalents thereof known to those skilled in the art, and so forth.

As used herein, a "target site" is a specific site or location within or present on a subject or patient. For example, a "target site" can refer to, but is not limited to a cell, population of cells, organ, tissue, tumor, or cancer cell. In some aspects, organs include, but are not limited to, lung, brain, pancreas, abdominal organs (e.g. stomach, intestine), ovary, breast, uterus, prostate, bladder, liver, colon, or kidney. In some aspects, a cell or population of cells include, but are not limited to, lung cells, brain cells, pancreatic cells, abdominal cells, ovarian cells, liver cells, colon cells, or kidney cells. In some aspects, a "target site" can be a tumor target site.

A "tumor target site" is a site or location within or present on a subject or patient that comprises or is adjacent to one or more cancer cells, previously comprised one or more tumor cells, or is suspected of comprising one or more tumor cells. For example, a tumor target site can refer to a site or location within or present on a subject or patient that is prone to metastases. Additionally, a target site or tumor target site can refer to a site or location of a resection of a primary tumor within or present on a subject or patient. Additionally, a target site or tumor target site can refer to a site or location adjacent to a resection of a primary tumor within or present on a subject or patient.

As used herein, an "alternating electric field" or "alternating electric fields" refers to a very-low-intensity, directional, intermediate-frequency alternating electrical fields delivered to a subject, a sample obtained from a subject or to a specific location within a subject or patient (e.g. a target site or a tumor target site). In some aspects, the alternating electrical field can be in a single direction or multiple directional.

An example of an alternating electric field includes, but is not limited to, a tumor-treating field. In some aspects, TTFields can be delivered through two pairs of transducer arrays that generate perpendicular fields within the treated tumor. For example, for the Optune™ system (a TTField delivery system) one pair of electrodes is located to the left and right (LR) of the tumor, and the other pair of electrodes is located anterior and posterior (AP) to the tumor. Cycling the field between these two directions (i.e., LR and AP) ensures that a maximal range of cell orientations is targeted.

As described herein, TTFields have been established as an anti-mitotic cancer treatment modality because they interfere with proper micro-tubule assembly during metaphase and eventually destroy the cells during telophase, cytokinesis, or subsequent interphase. TTFields target solid tumors and is described in U.S. Pat. No. 7,565,205, which is incorporated herein by reference in its entirety for its teaching of TTFields.

In-vivo and in-vitro studies show that the efficacy of TTFields therapy increases as the intensity of the electrical field increases. Therefore, optimizing array placement on the patient's scalp to increase the intensity in the diseased region of the brain is standard practice for the Optune system. Array placement optimization may be performed by "rule of thumb" (e.g., placing the arrays on the scalp as close to the tumor as possible), measurements describing the geometry of the patient's head, tumor dimensions, and/or tumor location. Measurements used as input may be derived from imaging data. Imaging data is intended to include any type of visual data, such as for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electrical field distributes within the head as a function of the positions of the array and, in some aspects, take account for variations in the electrical property distributions within the heads of different patients. The term "subject" refers to the target of administration, e.g. an animal. Thus, the subject of the disclosed methods can be a vertebrate, such as a mammal. For example, the subject can be a human. The term does not denote a particular age or sex. Subject can be used interchangeably with "individual" or "patient." For example, the target of administration can mean the recipient of the alternating electrical field.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Nanoparticles

Disclosed herein are methods involving nanoparticles. Any of the nanoparticles described herein can be used for one or more of the disclosed methods.

In some aspects, the nanoparticle can comprise a conducting or semi-conducting material. For example, the nanoparticle can comprise or consist of carbon gold, ferrous iron, selenium, silver, copper, platinum, iron oxide, graphene, iron dextran, superparamagnetic iron oxide, boron-doped detonation nanodiamonds, or a combination thereof. In some aspects, the nanoparticle can comprise an alloy selected from Au/Ag, Au/Cu, Au/Ag/Cu, Au/Pt, Au/Fe, Au/Cu or Au/F/Cu.

In some aspects, the nanoparticle can be a conductive nanoparticle. A conductive nanoparticle can increase conductivity and lower impedance in a target site or tumor target site. Thus, in some aspects of the disclosed methods, the impedance in a target site or tumor target site is lowered and/or the conductivity in a target site or tumor target site is increased.

In some aspects, the nanoparticle is a non-conductive nanoparticle. In some aspects, the non-conductive nanoparticle is a ferroelectric nanoparticle. Ferroelectric nanoparticles have emerged as promising tools for enhancing electric stimulation of cells and tissues. Several nanotransducers have been revealed to mediate photodynamic and magneto-thermal conversions, and to locally deliver anticancer stimuli to tumor burden in the field of nanooncology. Cell and tissue penetration of these nanotransducers could be controlled by remote electrical stimulation. Among ferroelectric nanoparticles, barium titanate nanoparticles (BTNPs) have high dielectric constants and suitable piezoelectric characteristics with high biocompatibility. Such non-conductive nanoparticles can be used in the methods disclosed herein to be taken up by a cell via TTField stimulation and to promote the antitumor action of TTFields by enhancing cell cycle-related apoptosis in cancer cells. In some aspects, the non-conductive nanoparticle is not a ferroelectric nanoparticle. A non-conductive nanoparticle can decrease conductivity and increase impedance in a target site or tumor target site. Thus, in some aspects of the disclosed methods, the impedance in a target site or tumor target site is increased and/or the conductivity in a target site or tumor target site is decreased.

In some aspects, a population of nanoparticles can be used in the methods disclosed herein. In some aspects, the population of nanoparticles can include conductive and non-conductive nanoparticles.

Nanoparticles (NPs) internalization into cells is known to be dependent on particle size and its zeta potential. NPs under 200 nm can be engulfed by cancer cells through clathrin-dependent pathway or macro-pinocytosis pathway. In some aspects, the size of the nanoparticle can be between 0.5 nm and 100 nm. In some aspects, the size of the nanoparticle can be between 0.5 nm & 2.5 nm. In some aspects, the size of the nanoparticle can be between 100 nm and 200 nm. In some aspects, the size of the nanoparticle can be greater than 100 nm. In some aspects, the disclosed methods allow for the use of nanoparticles (e.g. metal/magnetic), in a size range of 100 nm–200 nm (preferentially up to 150 nm to avoid accumulation in the liver and spleen), to target cancer cells in vivo.

In some aspects, the nanoparticle has a three-dimensional shape. For example, the nanoparticle can be a nanocube, nanotube, NanoBipyramid, NanoPlate, NanoCluster, Nanochaine, NanoStar, NanoShuttle, NanoHollow, dendrimer, nanorod, nanoshell, nanocage, nanosphere, nanofiber, or nanowire, or a combination thereof.

In some aspects, the nanoparticle can be mesoporous or nonporous.

In some aspects, the nanoparticle can be coated with a polysaccharide, poly amino acid, or synthetic polymer. Suitable coating for the nanoparticle can be chosen to decrease the toxicity of the nanoparticle and can provide the nanoparticle with the capacity for selective interaction with different types of cells and biological molecules. Suitable coating for the nanoparticle can be chosen to improve the nanoparticle biocompatibility and solubility in water and biological fluids by decreasing their aggregation capacity or increasing their stability, Suitable coating for the nanoparticle can be chosen to influence the nanoparticle pharmacokinetics, changing the patterns of the nanoparticle and/or distribution and accumulation in the body.

In some aspects, the nanoparticles can be incorporated into a scaffold prior to introducing the nanoparticles to the subject. In some aspects, the nanoparticles can be loaded onto or within a scaffold prior to or after introducing the scaffold to a subject. For example, a scaffold could be surgically provided to a subject and subsequently one or more of the nanoparticles described herein could be administered to the subject under conditions that allow for the nanoparticles to incorporate into the scaffold. Alternatively, nanoparticles could be incorporated into a scaffold outside of a subject and then the nanoparticle loaded scaffold could be surgically provided to a subject.

Examples of scaffolds include, but are not limited to scaffolds comprising natural polymers such as hyaluronic acid, fibrin, chitosan, and collagen. Examples of scaffolds include, but are not limited to scaffolds comprising synthetic polymers such as Polyethylene Glycol (PEG), polypropylene fumarate (PPF), polyanhydride, polycaprolactone (PCL), polyphosphazene, polyether ether ketone (PEEK), polylactic acid (PLA), and poly (glycolic acid) (PGA).

In some aspects, the nanoparticle is conjugated to one or more ligands. In some aspects, the one or more ligands can be conjugated to the nanoparticle via a linker. In some aspects, a linker comprises a thiol group, a C2 to C12 alkyl group, a C2 to C12 glycol group or a peptide. In some aspects, the linker comprises a thiol group represented by the general formula HO—(CH)n,—S—S—(CH2)m-OH wherein n and m are independently between 1 and 5. In some aspects, the one or more ligands are a small molecule, nucleic acid, carbohydrate, lipid, peptide, antibody, antibody fragment, or a therapeutic agent. For example the one or more ligands can be, but are not limited to, an anticancer drug, a cytotoxic drug, pain-management drug, pseudomonas exotoxin A, a non-radioactive isotope (e.g. boron-10 for boron neutron capture therapy), or a photosensitizer (e.g. photofrin, foscan, 5-aminolevulinic acid, Mono-L-aspartyl chlorin e6, pthalocyanines, Meta-tetra(hydroxyphenyl)porphyrins, texaphyrins, Tin ethyl etipurpurin).

In some aspects, the nanoparticle can be a labeled nanoparticle. In some aspects, labeled nanoparticles can be magnetic nanoparticles, nanoparticles decorated with Gd3+, nanoparticles decorated radioisotopes (e.g. technetium-99m, iodine-123, iodine-131, fluorine-18 carbon-11, nitrogen-13, oxygen-15, gallium-68, zirconium-89, and rubidium-82), nanoparticles decorated with a fluorescent label (e.g. Quantum dots), nanoparticles decorated with photosensitizer (e.g. photofrin, foscan, 5-aminolevulinic acid, Mono-L-aspartyl chlorin e6, pthalocyanines, Meta-tetra(hydroxyphenyl)porphyrins,texaphyrins, Tin ethyl etipurpurin), nanoparticles decorated with dye. In some aspects, the nanoparticle can be coated with a labeled antibody and therefore the nanoparticle is indirectly labeled. In some aspects, if there are size constraints, the nanoparticles, if decorated or conjugated to a large moiety, can be of a smaller size to accommodate a larger moiety.

Other examples of nanoparticles include, but are not limited to, silica nanoparticles, hydrophilic polymers (e.g. polyacrylamide (PAA), polyurethanes, poly(hydroxyethyl methacrylamide) (pHEMA), certain poly(ethylene glycols), and hydrophobic polymers (e.g. polystyrene nanoparticles).

In some aspects, the nanoparticle can be introduced into a target site. In some aspects, the nanoparticle can be introduced into a tumor target site. In some aspects, the nanoparticle can be introduced into a tumor or cancer cell. In some aspects, the nanoparticle can be introduced into a location in a subject suspected of comprising one or more tumor cells. In some aspects, the nanoparticle can be introduced into to a site or location within or present on a subject or patient that is prone to metastases. In some aspects, the nanoparticle can be introduced into to a site or location of a resection of a primary tumor within or present on a subject or patient. In some aspects, the nanoparticle can be introduced into the tumor or cancer cell via injection post primary tumor resection. In some aspects, the nanoparticle can be introduced into a site adjacent to a target site. In some aspects, the nanoparticle can be introduced into a site adjacent to a location in a subject suspected of comprising one or more tumor cells.

In some aspects, the nanoparticle can be introduced into a tumor target site, wherein the tumor target site adjacent to a tumor target site. In some aspects, the nanoparticle can be introduced into a tumor target site, wherein the tumor target site is adjacent to a tumor or cancer cell. In some aspects, the nanoparticle can be introduced into a tumor target site, wherein the tumor target site adjacent to a location in a subject suspected of comprising one or more tumor cells. In some aspects, the nanoparticle can be introduced into a tumor target site, wherein the tumor target site adjacent to a site or location within or present on a subject or patient that is prone to metastases. In some aspects, the nanoparticle can be introduced into a tumor target site, wherein the tumor target site adjacent to a site or location of a resection of a primary tumor within or present on a subject or patient. In some aspects, the nanoparticle can be introduced into a tumor target site, wherein the tumor target site adjacent to the tumor or cancer cell via injection post primary tumor resection. In some aspects, the nanoparticle can be introduced into a tumor target site, wherein the tumor target site adjacent to the tumor or cancer cell via intratumor injection (e.g. computed tomography-guided, during surgery or biopsy).

In some aspects, the nanoparticle can be introduced intratumorally, intracranially, intraventricularly, intrathecally, epidurally, intradurally, intravascularly, intravenously (targeted or non-targeted), intraarterially, intramuscularly, subcutaneously, intraperitoneally, orally, intranasally, via intratumor injection (e.g. computed tomography-guided, during surgery or biopsy) or via inhalation. In some aspects, nanoparticles can be targeted to the tumor or tumor target site using tumor-targeting moieties. Tumor-targeting moieties can be, but are not limited to, folate, transferrin, aptamers, antibodies, nucleic acids and peptides. Thus, in some aspects, the nanoparticle can be introduced to the subject in a targeted or non-targeted manner.

In some aspects, the nanoparticle can be introduced at a concentration based on tumor volume, method of delivery, limitations of the device administering the alternating electric field, patient weight, patient age, size of tumor, the type of tumor or cancer, location of the tumor or cancer cells, age of the patient, or any other physical or genotypic attribute of the patient, cancer cell or tumor. In some aspects, the size of the nanoparticles can be used to determine the concentration of the nanoparticles to be introduced. In some aspects, the nanoparticle can be introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 ng per $mm^3$ tumor. In some aspects, the nanoparticle can be introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 µg.

In some aspects, the nanoparticle can be introduced to the subject once, twice, or three or more times.

1. Pharmaceutical Compositions

Disclosed herein are pharmaceutical compositions comprising one or more of the nanoparticles described herein. In some aspects, the nanoparticles described herein can be provided in a pharmaceutical composition. For example, the nanoparticles described herein can be formulated with a pharmaceutically acceptable carrier.

In some aspects, a pharmaceutical composition can comprise a chemotherapeutic agent. In some aspects, a pharmaceutical composition can comprise a chemotherapeutic agent and one or more of the nanoparticles described herein. For example, disclosed herein are pharmaceutical compositions comprising one or more of the nanoparticles described herein and an anticancer drug, a cytotoxic drug, pain-management drug, pseudomonas exotoxin A, a non-radioactive isotope (e.g. boron-10 for boron neutron capture therapy), and/or a photosensitizer (e.g. photofrin, foscan, 5-aminolevulinic acid, Mono-L-aspartyl chlorin e6, pthalocyanines, Meta-tetra(hydroxyphenyl)porphyrins,texaphyrins, Tin ethyl etipurpurin).

Disclosed herein are compositions comprising one or more of the nanoparticles described herein that that further comprise a carrier such as a pharmaceutically acceptable carrier. For example, disclosed are pharmaceutical compositions, comprising the nanoparticles disclosed herein, and a pharmaceutically acceptable carrier.

For example, the nanoparticles described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of nanoparticle being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

In the methods described herein, delivery (or administration or introduction) of the nanoparticles or pharmaceutical compositions disclosed herein to subjects can be via a variety of mechanisms.

C. Altering Impedance in a Target Site

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered, wherein the current density and/or power loss density in the target site of the subject to the alternating current is altered.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered and wherein the conductivity is decreased in the site adjacent to the target site.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered and wherein the impedance in the site adjacent to the target site is increased.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered and wherein the conductivity is increased in the target site.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered and wherein the impedance in the target site is decreased.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered and wherein the non-conductive nanoparticle is not a ferroelectric nanoparticle.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered and wherein the method further comprises introducing a nanoparticle to a target site in the subject and applying an alternating electric field to the target site of the subject. In some aspects, the impedance in the target site is lowered and/or the conductivity in the target site is increased.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered, wherein the nanoparticle is a non-conductive nanoparticle. In some aspects, the impedance in the target site is increased and/or conductivity in the target site is decreased.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered, wherein the alternating electric field is a tumor-treating field.

Disclosed are methods of altering the electric impedance to an alternating electric field in a site adjacent to a target site of a subject, comprising: introducing a non-conductive nanoparticle to a site adjacent to the target site in the subject; and applying an alternating electric field to the site adjacent to the target site of the subject, wherein the electric impedance in the site of the subject to the alternating current is altered, wherein the target site is a tumor target site. In some aspects, the altered electric impedance in the target site of the subject to the alternating current results in an increased mitotic effect of the alternating electric field in the target site.

Disclosed herein are methods of altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered.

Disclosed herein are methods of altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the impedance in the target site is lowered and/or wherein the conductivity in the target site is increased.

Disclosed herein are methods of altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the method further comprises introducing a non-conductive nanoparticle to a site adjacent to the target site in the subject; and applying an alternating electric field to the site adjacent to the target site of the subject. In some aspects, the current density and/or power loss density in the target site of the subject to the alternating current is altered. In some aspects, the conductivity is decreased in the site adjacent to the target site. In some aspects, the impedance in the site adjacent to the target site is increased. In some aspects, the conductivity is increased in the target site. In some aspects, the impedance in the target site is decreased.

Disclosed herein are methods of altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the non-conductive nanoparticle is not a ferroelectric nanoparticle. In some aspects, the impedance in the target site is increased and/or the conductivity in the target site is decreased.

Disclosed herein are methods of altering the electric impedance to an alternating electric field in a target site of a subject, comprising: introducing a conductive nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered, wherein the alternating electric field is a tumor-treating field. In some aspects, the nanoparticles are nanoparticles that increase tissue permittivity. In some aspects, the target site is a tumor target site. In some aspects, the altered electric impedance in the tumor target site of the subject to the alternating current results in an increased mitotic effect of the alternating electric field in the tumor target site.

Disclosed are methods of altering the electric impedance to an alternating electric field in a target site of a subject, comprising introducing a nanoparticle to a target site in the subject; and applying an alternating electric field to the target site of the subject, wherein the electric impedance in the target site of the subject to the alternating current is altered.

Disclosed are methods of altering the electric impedance to an alternating electric field in a tumor target site of a subject, comprising introducing a nanoparticle to a tumor target site in the subject; and applying an alternating electric field to the tumor target site of the subject, wherein the electric impedance in the tumor target site of the subject to the alternating current is altered.

Disclosed are methods of altering the electric impedance to an alternating electric field in a tumor target site of a subject, comprising introducing a nanoparticle to a tumor target site in the subject; and applying an alternating electric field to the tumor target site of the subject, wherein the electric impedance in the tumor target site of the subject to the alternating current is altered, wherein the tumor target site is adjacent to one or more cancer cells, previously comprised one or more tumor cells, or is suspected of comprising one or more tumor cells. Disclosed are methods of altering the electric impedance to an alternating electric field in a target site of a subject, comprising introducing a nanoparticle to a target site in the subject; and applying an alternating electric field to the target site of the subject, wherein the electric impedance in the target site of the subject to the alternating current is altered, wherein the current density and/or power loss density in the target site of the subject to the alternating current is altered. Disclosed are methods of altering the electric impedance to an alternating electric field in a tumor target site of a subject, comprising introducing a nanoparticle to a tumor target site in the subject; and applying an alternating electric field to the tumor target site of the subject, wherein the electric impedance in the tumor target site of the subject to the alternating current is altered, wherein the current density and/or power loss density in the tumor target site of the subject to the alternating current is altered.

Disclosed are methods of altering the electric impedance to an alternating electric field in a tumor target site of a subject, comprising introducing a nanoparticle to a tumor target site in the subject; and applying an alternating electric field to the tumor target site of the subject, wherein the electric impedance in the tumor target site of the subject to the alternating current is altered, wherein the current density and/or power loss density in the tumor target site of the subject to the alternating current is altered, wherein the tumor target site is adjacent to one or more cancer cells, previously comprised one or more tumor cells, or is suspected of comprising one or more tumor cells.

In some aspects, the current density in the target site or tumor target site is increased. In some aspects, the current density is in the target site or tumor target site decreased. In some aspects, power loss density in the target site or tumor target site is increased. In some aspects, power loss density in the target site or tumor target site is decreased.

In some aspects, the nanoparticle is a conductive nanoparticle. In some aspects, a conductive nanoparticle can increase conductivity and lower impedance in the target site or tumor target site. Thus, in some aspects of the disclosed methods, the impedance in the target site or tumor target site is lowered and/or the conductivity in the target site or tumor target site is increased.

In some aspects, the nanoparticle is a non-conductive nanoparticle. In some aspects, the non-conductive nanoparticle is not a ferroelectric nanoparticle. In some aspects, a non-conductive nanoparticle can decrease conductivity and increase impedance in the target site or tumor target site. Thus, in some aspects of the disclosed methods, the impedance in the target site or tumor target site is increased and/or the conductivity in the target site or tumor target site is decreased.

In some aspects, a population of nanoparticles can be used in the methods disclosed herein. In some aspects, the population of nanoparticles can include conductive and non-conductive nanoparticles.

In some aspects, the alternating electric field used in the methods disclosed herein is a tumor-treating field. In some aspects, the alternating electric field (e.g. tumor-treating field) can vary dependent on the type of cancer or tumor being treated. In some aspects, the cancer cells are glioblastoma cells, uterine sarcoma cells, breast adenocarcinoma cells, pancreatic cancer cells, non-small cell lung cancer, hepatocellular, gastric cancer cells, brain cancer cells kidney cancer cells, neuroblastoma cells, colon cancer cells, bladder cancer cells, prostate cancer cells, or thymus cancer cells. In some aspects, the frequency of the alternating electric fields can be 200 kHz. The frequency of the alternating electric fields can also be, but is not limited to, about 200 kHz, between 50 and 500 kHz, between 100 and 500 kHz, between 25 kHz and 1 MHz, between 50 and 190 kHz, between 25 and 190 kHz, or between 210 and 400 kHz.

In some aspects, the field strength of the alternating electric fields can be between 1 and 4 V/cm RMS. In some aspects, different field strengths can be used (e.g., between 0.1 and 10 V/cm).

In some aspects, the alternating electric fields can be applied for a variety of different intervals ranging from 0.5 hours to 72 hours. In some aspects, a different duration can be used (e.g., between 0.5 hours and 14 days). In some aspects, application of the alternating electric fields can be repeated periodically. For example, the alternating electric fields can be applied every day for a two hour duration.

In some aspects, the nanoparticles are nanoparticles that increase tissue or cell permittivity.

In some aspects, the altered electric impedance in the target site or tumor target site of the subject to the alternating current results in an increased anti mitotic effect of the alternating electric field in the target site. For example, the increased anti mitotic effect can refer to interference with proper micro-tubule assembly during metaphase which can eventually destroy the cells (e.g. cancer cells) present in or at the target site during telophase, cytokinesis, or subsequent interphase.

Disclosed are methods of altering the electric impedance in a target site or tumor target site with one frequency that allows nanoparticles to enter into cells in the target site or tumor target site and then applying a second frequency to the target site or tumor target site wherein the electric impedance to the second frequency in the target site or tumor target site is altered. Disclosed are methods of altering the electric impedance in a target site or tumor target site with one frequency (a first frequency) that allows nanoparticles to enter into cells in the target site or tumor target site and then applying a second frequency to the target site or tumor target site wherein the electric impedance to the second frequency in the target site or tumor target site is altered, further comprising applying multiple first and second frequencies. For example, disclosed are methods of altering the electric impedance to an alternating electric field in a target site or tumor target site of a subject, comprising applying a first alternating electric field at a first frequency to the target site or tumor target site for a first period of time, wherein application of the first alternating electric field at the first frequency to the target site or tumor target site for the first period of time increases permeability of cell membranes of the cells present in the target site or tumor target site; introducing a nanoparticle to the target site or tumor target site, wherein the increased permeability of the cell membranes enables the nanoparticle to cross the cell membranes; and applying a second alternating electric field at a second frequency to the target site or tumor target site for a second period of time, wherein the second frequency is different from the first frequency, and wherein the impedance in the target site or tumor target site of the subject of the second alternating electric field at the second frequency is altered. In some aspects, the current density and/or power loss density in the target site or tumor target site of the subject to the alternating current is altered. In some aspects, the cells are cancer cells. In some aspects, the cancer cells are glioblastoma cells, uterine sarcoma cells, breast adenocarcinoma cells, pancreatic cancer cells, non-small cell lung cancer, hepatocellular, gastric cancer cells, or brain cancer cells. In some aspects, the cancer cells comprise glioblastoma cells, the first frequency is between 250 kHz and 350 kHz, and the second frequency is between 150 kHz and 250 kHz. In some aspects, the cancer cells comprise uterine sarcoma cells, the first frequency is between 125 kHz and 175 kHz, and the second frequency is between 75 kHz and 125 kHz. In some aspects, the cancer cells comprise breast adenocarcinoma cells, the first frequency is between 75 kHz and 175 kHz, and the second frequency is between 100 kHz and 300 kHz. In some aspects, the step of introducing the nanoparticle begins at a given time, and wherein the step of applying the first alternating electric field ends at least 12 hours after the given time. In some aspects, the step of applying the first alternating electric field begins at least one hour before the given time. In some aspects, the second period of time comprises a plurality of non-contiguous intervals of time during which the second alternating electric field at the second frequency is applied to the cancer cells, wherein the plurality of non-contiguous intervals of time collectively add up to at least one week.

Disclosed are methods of altering the electric impedance to an alternating electric field in a target site or tumor target site of a subject, comprising applying a first alternating electric field at a first frequency to the target site or tumor target site for a first period of time, wherein application of the first alternating electric field at the first frequency to the target site or tumor target site for the first period of time increases permeability of cell membranes of the cells present in the target site or tumor target site; introducing a nanoparticle to the target site or tumor target site, wherein the increased permeability of the cell membranes enables the nanoparticle to cross the cell membranes; and applying a second alternating electric field at a second frequency to the target site or tumor target site for a second period of time, wherein the second frequency is different from the first frequency, and wherein the impedance in the target site or tumor target site of the subject of the second alternating electric field at the second frequency is altered, wherein the target site or tumor target site is adjacent to one or more cancer cells, previously comprised one or more tumor cells, or is suspected of comprising one or more tumor cells. In some aspects, the current density and/or power loss density in the target site or tumor target site of the subject to the alternating current is altered. In some aspects, the second alternating electric field is a tumor-treating field. In some aspects, the cells are cancer cells. In some aspects, the cancer cells are glioblastoma cells, uterine sarcoma cells, breast adenocarcinoma cells, pancreatic cancer cells, non-small cell lung cancer, hepatocellular, gastric cancer cells, or brain cancer cells. In some aspects, the cancer cells comprise glioblastoma cells, the first frequency is between 250 kHz and 350 kHz, and the second frequency is between 150 kHz and 250 kHz. In some aspects, the cancer cells comprise uterine sarcoma cells, the first frequency is between 125 kHz and 175 kHz, and the second frequency is between 75 kHz and 125 kHz. In some aspects, the cancer cells comprise breast adenocarcinoma cells, the first frequency is between 75 kHz and 175 kHz, and the second frequency is between 100 kHz and 300 kHz. In some aspects, the step of introducing the nanoparticle begins at a given time, and wherein the step of applying the first alternating electric field ends at least 12 hours after the given time. In some aspects, the step of applying the first alternating electric field begins at least one hour before the given time. In some aspects, the second period of time comprises a plurality of non-contiguous intervals of time during which the second alternating electric field at the second frequency is applied to the cancer cells, wherein the plurality of non-contiguous intervals of time collectively add up to at least one week.

Also discussed herein are methods of using heat, or hyperthermia, to kill or ablate cells in a target site or tumor target cite. For example, the methods disclosed herein can use one or more of the nanoparticles disclosed herein, wherein the nanoparticles are introduced into a cell in a target site or tumor target site, and then exposed to an alternating electric field or alternating magnetic field (AMF). Exposure of the cells in the target site or tumor target site to the alternating electric field or magnetic field (AMF) can cause the nanoparticles to heat (e.g. hit temperatures exceeding 100 degrees Fahrenheit), which can result in the killing the cells in the target site or tumor target site.

Disclosed are methods of killing or ablating cells in a target site or tumor target site with one frequency that allows nanoparticles to enter into cells in the target site or tumor target site and then applying an alternating electric field or alternating magnetic field to the target site or tumor target site, wherein the nanoparticles convert the alternating electric field or alternating magnetic field into thermal energy, thereby killing or ablating the cells in the target site or tumor target site. In some aspects, the methods disclosed herein ca further comprise applying multiple first and second frequencies.

For example, disclosed are methods of ablating or killing cells in a target site or tumor target site of a subject, comprising applying a first alternating electric field at a first frequency to the target site or tumor target site for a first period of time, wherein application of the first alternating electric field at the first frequency to the target site or tumor target site for the first period of time increases permeability of cell membranes of the cells present in the target site or tumor target site; introducing a nanoparticle to the target site or tumor target site, wherein the increased permeability of the cell membranes enables the nanoparticle to cross the cell membranes; and applying a second alternating electric field at a second frequency or an alternating magnetic field to the target site or tumor target site for a second period of time, wherein one or more cells present in the target site or tumor target site are killed or ablated. In some aspects, the second alternating electric field is a tumor-treating field. In some aspects, the target site or tumor target site is adjacent to one or more cancer cells, previously comprised one or more tumor cells, or is suspected of comprising one or more tumor cells. In some aspects, the current density and/or power loss density in the target site or tumor target site of the subject to the alternating current is altered. In some aspects, the second alternating electric field is a tumor-treating field.

In any of the methods disclosed herein, the methods can further comprise administering to the subject an anticancer drug, a cytotoxic drug, pain-management drug, pseudomonas exotoxin A, a non-radioactive isotope (e.g. boron-10 for boron neutron capture therapy), a photosensitizer (e.g. photofrin, foscan, 5-aminolevulinic acid, Mono-L-aspartyl chlorin e6, pthalocyanines, Meta-tetra(hydroxyphenyl)porphyrins,texaphyrins, Tin ethyl etipurpurin), or applying or exposing the subject to an electronic system for influencing cellular functions. For example, in any of the methods disclosed herein, a subject can be exposed to or a system can be applied to the subject wherein the system includes one or more controllable low energy HF (High Frequency) carrier signal generator circuits, one or more data processors for receiving control information, one or more amplitude modulation control generators and one or more amplitude modulation frequency control generators. In some aspects, the amplitude modulation frequency control generators are adapted to accurately control the frequency of the amplitude modulations to within an accuracy of at least 1000 ppm, most preferably to within about 1 ppm, relative to one or more determined or predetermined reference amplitude modulation frequencies. Additional embodiments and specific frequencies for particular cancers are described in U.S. Pat. No. 8,977,365, which is hereby incorporated by reference in its entirety for it teaching of systems and methods useful for influencing cellular functions or malfunctions in a subject.

D. Increasing Antitumor Activity of TTF by Altering Electric Field's Distribution Utilizing Nanoparticles Disclosed herein are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased.

Disclosed herein are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the magnitude of the current density of the alternating electric field is increased in the target site.

Disclosed herein are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the impedance in the target site is lowered.

Disclosed herein are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the conductivity in the target site is increased and/or wherein the impedance in the site adjacent to the target site is increased.

Disclosed herein are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the alternating electric field is a tumor-treating field.

Disclosed herein are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the efficacy of the alternating electric field in the target site of the subject is increased, wherein the target site is a tumor target site.

Disclosed herein are methods of increasing the efficacy of an alternating electric field in a target site of a subject, the method comprising: introducing a non-conductive nanoparticle to a site adjacent to the target site in the subject; introducing a conductive nanoparticle to a target site in the subject; applying an alternating electric field to the target site and the site adjacent to the target site of the subject, wherein the increased efficacy of the alternating electric field in the target site results in an increased anti-mitotic effect of the alternating electric field in the target site.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the nanoparticle is a non-conductive nanoparticle.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the impedance in the non-target site adjacent to the target site is increased and/or wherein the conductivity in the non-target site adjacent to the target site is decreased.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the impedance in the target site is lowered and/or wherein the conductivity in the target site is increased.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the magnitude of the current density of the alternating electric field is decreased in the non-target site adjacent to the target site.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, further comprising introducing a conductive nanoparticle to the target site in in the subject. In some aspects, the impedance in the target site is lowered.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the alternating electric field is a tumor-treating field.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the efficacy of the alternating electric field in the target site of the subject is increased, wherein the target site is a tumor target site. In some aspects, the increased efficacy of the alternating electric field in the target site results in an increased mitotic effect of the alternating electric field in the target site. In some aspects, the nanoparticle is introduced into the tumor. In some aspects, the nanoparticle is introduced into the tumor via injection post primary tumor resection. In some aspects, the nanoparticle is introduced into the tumor via intratumor injection (e.g. computed tomography-guided, during surgery or biopsy).

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced intratumorally, intracranially, intraventricularly, intrathecally, epidurally, intradurally, intravascularly, intravenously (targeted or non-targeted), intraarterially, intramuscularly, subcutaneously, intraperitoneally, orally, intranasally, via intratumor injection (e.g. computed tomography-guided, during surgery or biopsy) or via inhalation.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced to the subject in a targeted or non-targeted manner.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 ng per mm$^3$ tumor.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced at about 0.001 to 0.01, 0.01 to 0.1, 0.1 to 0.5, 0.5 to 5, 5 to 10, 10 to 20, 20 to 50, 50 to 100, 100 to 200, 200 to 300, 300 to 400, 400 to 500, 500 to 600, 600 to 700, 700 to 800, 800 to 900, or 900 to 1000 µg.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle is introduced once, twice, three or more times.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the conductive nanoparticle comprises or consists of carbon gold, ferrous iron, selenium, silver, copper, platinum, iron oxide, graphene, iron dextran, superparamagnetic iron oxide, boron-doped detonation nanodiamonds, or a combination thereof. In some aspects, the conductive nanoparticle comprises an alloy selected from Au/Ag, Au/Cu, Au/Ag/Cu, Au/Pt, Au/Fc, Au/Cu or Au/Fe/Cu.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is between 0.5 nm and 100 nm.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is between 0.5 nm and 2.5 nm.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is greater than 100 nm.

Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the size of the nanoparticle is between 100 nm and 200 nm, Disclosed herein are methods of increasing the efficacy of an alternating electric field in a target site of a subject, the method comprising: introducing a non-conductive nanoparticle to a site adjacent to the target site in the subject; applying an alternating electric field to the site adjacent to the target site or to the target site of the subject, wherein the nanoparticle has a three-dimensional shape. In some aspects, the nanoparticle is a nanocube, nanotube, NanoBipyramid, NanoPlate, NanoCluster, Nanochaine, NanoStar, NanoShuttle, NanoHollow, dendrimer, nanorod, nanoshell, nanocage, nanosphere, nanofiber, or nanowire, or a combination thereof. In some aspects, the nanoparticle is mesoporous or nonporous. In some aspects, the nanoparticle is coated with a polysaccharides, poly amino acid, or synthetic polymer.

In some aspects, the nanoparticle is incorporated into a scaffold prior to introducing the nanoparticle to the subject.

In some aspects, the nanoparticles are loaded onto or within a scaffold.

In some aspects, the nanoparticle is provided in a pharmaceutical composition.

In some aspects, the pharmaceutical composition further comprises a chemotherapeutic agent.

In some aspects, the nanoparticle is conjugated to one or more ligands. In some aspects, the one or more ligands are be conjugated to the nanoparticle via a linker. In some aspects, the linker comprises a thiol group, a C2 to C12 alkyl group, a C2 to C12 glycol group or a peptide. In some aspects, the linker comprises a thiol group represented by the general formula HO—(CH)n,—S—S—(CH2)m-OH wherein n and m are independently between 1 and 5.

In some aspects, the one or more ligands are a small molecule, nucleic acid, carbohydrate, lipid, peptide, antibody, antibody fragment, or a therapeutic agent. In some aspects, the one or more ligands are an anticancer drug or a cytotoxic drug.

Disclosed are methods of increasing the efficacy of an alternating electric field in a target site of a subject, the method comprising introducing a nanoparticle to a target site in the subject; applying an alternating electric field to the target site of the subject, wherein the efficacy of the alternating electric field in the target site of the subject is increased.

Disclosed are methods of increasing the efficacy of an alternating electric field in a tumor target site of a subject, the method comprising introducing a nanoparticle to a tumor target site in the subject; applying an alternating electric field to the tumor target site of the subject, wherein the efficacy of the alternating electric field in the tumor target site of the subject is increased.

Disclosed are methods of increasing the efficacy of an alternating electric field in a tumor target site of a subject, the method comprising introducing a nanoparticle to a tumor target site in the subject; applying an alternating electric field to the tumor target site of the subject, wherein the efficacy of the alternating electric field in the tumor target site of the subject is increased, wherein the tumor target site is adjacent to one or more cancer cells, previously comprised one or more tumor cells, or is suspected of comprising one or more tumor cells.

Disclosed are methods of increasing the efficacy of an alternating electric field in a target site of a subject, the method comprising introducing a nanoparticle to a target site in the subject; applying an alternating electric field to the target site of the subject, wherein the efficacy of the alternating electric field in the target site of the subject is increased, wherein the magnitude of the current density of the alternating electric field is increased in the target site.

Disclosed are methods of increasing the efficacy of an alternating electric field in a tumor target site of a subject, the method comprising introducing a nanoparticle to a tumor target site in the subject; applying an alternating electric field to the tumor target site of the subject, wherein the efficacy of the alternating electric field in the tumor target site of the subject is increased, wherein the magnitude of the current density of the alternating electric field is increased in the tumor target site.

Disclosed are methods of increasing the efficacy of an alternating electric field in a tumor target site of a subject, the method comprising introducing a nanoparticle to a tumor target site in the subject; applying an alternating electric field to the tumor target site of the subject, wherein the efficacy of the alternating electric field in the tumor target site of the subject is increased, wherein the magnitude of the current density of the alternating electric field is increased in the tumor target site, wherein the tumor target site is adjacent to one or more cancer cells, previously comprised one or more tumor cells, or is suspected of comprising one or more tumor cells.

Disclosed are methods of increasing the efficacy of an alternating electric field in a target site of a subject, the method comprising introducing a nanoparticle to a target site in the subject; applying an alternating electric field to the target site of the subject, wherein the efficacy of the alternating electric field in the target site of the subject is increased and further comprising introducing a non-conductive nanoparticle to a non-target site adjacent to the target site in the subject. In some aspects, the target site is a tumor target site. In some aspects, the tumor target site is adjacent to one or more cancer cells, previously comprised one or more tumor cells, or is suspected of comprising one or more tumor cells Disclosed are methods of increasing the efficacy of an alternating electric field in a target site of a subject, the method comprising introducing a non-conductive nanoparticle to a site adjacent to a target site in the subject; applying an alternating electric field to the target site of the subject, wherein the efficacy of the alternating electric field in the target site.of the subject is increased. In some aspects, the target site is a tumor target site. In some aspects, the tumor target site is adjacent to one or more cancer cells, previously comprised one or more tumor cells, or is suspected of comprising one or more tumor cells.

In some aspects, the nanoparticle is a conductive nanoparticle. A conductive nanoparticle can increase conductivity and lower impedance in the target site or tumor target site. Thus, in some aspects of the disclosed methods, the impedance in the target site or tumor target site is lowered and/or the conductivity in the target site or tumor target site is increased.

In some aspects, the nanoparticle is a non-conductive nanoparticle. In some aspects, the non-conductive nanoparticle is not a ferroelectric nanoparticle. A non-conductive nanoparticle can decrease conductivity and increase impedance in the target site or tumor target site. Thus, in some aspects of the disclosed methods, the impedance in the target site or tumor target site is increased and/or the conductivity in the target site or tumor target site is decreased. In some aspects, the impedance in a site adjacent to the in the target site or tumor target site is increased and/or the conductivity in the site adjacent to the target site or tumor target site is decreased.

In some aspects, any of the nanoparticles disclosed herein can be used in the methods of increasing the efficacy of an alternating electric field in the target site or tumor target site of a subject disclosed herein.

In some aspects, the alternating electric field is a tumor-treating field as disclosed herein.

In some aspects, the alternating electric fields can be applied for a variety of different intervals ranging from 0.5 hours to 72 hours. In some aspects, a different duration can be used (e.g., between 0.5 hours and 14 days). In some aspects, application of the alternating electric fields can be repeated periodically. For example, the alternating electric fields can be applied every day for a two hour duration.

In some aspects, the increased efficacy of the alternating electric field in the target site or tumor target site results in an increased mitotic effect of the alternating electric field in the target site or tumor target site. For example, the increased mitotic effect can refer to interference with proper micro-tubule assembly during metaphase which can eventually destroy the cells (e.g. cancer cells) present in or at the target site or tumor target site during telophase, cytokinesis, or subsequent interphase.

In some aspects, the magnitude of the current density of the alternating electric field is decreased in a site adjacent to the target site or tumor target site.

E. Increasing Uptake of Nanoparticles

Disclosed are methods for improving the transport of a nanoparticle across a cell membrane of a cell, the method comprising applying an alternating electric field to the cell for a period of time, wherein application of the alternating electric field increases permeability of the cell membrane; and introducing the nanoparticle to the cell, wherein the increased permeability of the cell membrane enables the nanoparticle to cross the cell membrane. In some aspects, the cells are cancer or tumor cells. In some aspects, the cells are not cancer or tumor cells.

In some aspects, the methods of PCT/US19/40479 filed on Jul. 3, 2019 can be used in the methods disclosed herein. For example, PCT/US19/40479 filed on Jul. 3, 2019 describes methods and processes to deliver a substance across a cell membrane of a cell, which is hereby incorporated by reference for its teaching of same. For example, PCT/US19/40479 filed on Jul. 3, 2019 describes methods and processes to that comprises applying an alternating electric field to the cell for a period of time, wherein application of the alternating electric field increases permeability of the cell membrane; and introducing the substance to a vicinity of the cell, wherein the increased permeability of the cell membrane enables the substance to cross the cell membrane.

In some aspects, the nanoparticle delivered across a cell membrane of a cell is a conductive nanoparticle. In some aspects, the nanoparticle is a non-conductive nanoparticle. In some aspects, the non-conductive nanoparticle is not a ferroelectric nanoparticle. Thus, in some aspects the nanoparticle can be a non-ferroelectric nanoparticle.

In some aspects, any of the nanoparticles disclosed herein can be used in the disclosed methods for improving the transport of a nanoparticle across a cell membrane of a cell.

In some aspects, three methods for improving the transport of a nanoparticle across a cell membrane of a cell, the method comprises, in part, applying an alternating electric field to the cell for a period of time. In some aspects, an alternating electric field can be used to introduce the nanoparticle into cancer cells only. In some aspects, the alternating electric field can be applied at a frequency of about 200 kHz. In some aspects, the alternating electric field can be applied at a frequency between 50 and 190 kHz. In some aspects, the alternating electric field can be applied at a frequency between 210 and 400 kHz. In some aspects, the alternating electric field has a field strength of at least 1 V/cm RMS. In some aspects, the alternating electric field has a frequency between 50 and 190 kHz. In some aspects, the alternating electric field has a frequency between 210 and 400 kHz. In some aspects, the alternating electric field has a field strength of at least 1 V/cm RMS. In some aspects, the alternating electric field has a field strength between 1 and 4 V/cm RMS.

In some aspects, the step of introducing the nanoparticle begins at a given time, and wherein the step of applying the alternating electric field ends at least 12 hours after the given time. In some aspects, the step of applying the alternating electric field begins at least one hour before the given time. In some aspects, the step of applying the alternating electric field begins at least one to around twenty-four hours before the given time.

F. Increasing Uptake of Nanoparticles and Treating

Disclosed are methods of increasing cell permeability of a cell (e.g. a tumor or cancer cell) with one frequency that allows nanoparticles in to the cell and then applying a second frequency for treatment via tumor treating fields based on the presence of the nanoparticle in the cell. In some aspects, the methods disclosed herein ca further comprise applying multiple first and second frequencies. In some aspects, the first frequency can selected so as to maximize the openings in the cell membrane such that nanoparticles can pass through and the. In some aspects, the second frequency can be chosen to enhance the effect of a TTField on the cell.

Disclosed are methods for reducing the viability of a cell, the method comprising: applying a first alternating electric field at a first frequency to the cell for a first period of time, wherein application of the first alternating electric field at the first frequency to the cell for the first period of time increases permeability of cell membrane of the cancer cell; introducing a nanoparticle to the cell, wherein the increased permeability of the cell membrane of the cell enables the nanoparticle to cross the cell membrane; and applying a second alternating electric field at a second frequency to the cell for a second period of time, wherein the second frequency is different from the first frequency, and wherein the second alternating electric field at the second frequency reduces viability of the cell.

Disclosed are methods for reducing the viability of cancer cells, the method comprising: applying a first alternating electric field at a first frequency to the cancer cells for a first period of time, wherein application of the first alternating electric field at the first frequency to the cancer cells for the first period of time increases permeability of cell membranes of the cancer cells; introducing a nanoparticle to the cancer cells, wherein the increased permeability of the cell membranes enables the nanoparticle to cross the cell membranes; and applying a second alternating electric field at a second frequency to the cancer cells for a second period of time, wherein the second frequency is different from the first frequency, and wherein the second alternating electric field at the second frequency reduces viability of the cancer cells.

Disclosed are methods for reducing the viability of a cell, the method comprising: applying a first alternating electric field at a first frequency to a target site or tumor target site comprising the cell for a first period of time, wherein application of the first alternating electric field at the first frequency to the target site or tumor target site for the first period of time increases permeability of cell membranes of the cell; introducing a first nanoparticle to the cell, wherein the increased permeability of the cell membranes enables the first nanoparticle to cross the cell membrane; and applying a second alternating electric field at a second frequency to the target site or tumor target site for a second period of time, wherein the second frequency is different from the first frequency, and wherein the second alternating electric field at the second frequency reduces viability of the cell, and further comprising introducing a second nanoparticle to a site adjacent to the target site or tumor target site in the subject. In some aspects, the site adjacent to the target site or tumor target site in the subject can be any site adjacent to cell that do not contain cell. For example, the site adjacent to the target site or tumor target site in the subject can be any site adjacent to a cancer or tumor cell that do not contain the cancer or tumor cell.

Disclosed are methods for reducing the viability of cancer cells, the method comprising: applying a first alternating electric field at a first frequency to the cancer cells for a first period of time, wherein application of the first alternating electric field at the first frequency to the cancer cells for the first period of time increases permeability of cell membranes of the cancer cells; introducing a first nanoparticle to the cancer cells, wherein the increased permeability of the cell membranes enables the first nanoparticle to cross the cell membranes; and applying a second alternating electric field at a second frequency to the cancer cells for a second period of time, wherein the second frequency is different from the first frequency, and wherein the second alternating electric field at the second frequency reduces viability of the cancer cells, and further comprising introducing a second nanoparticle to a non-target site adjacent to the cancer cells in the subject. In some aspects, the non-target site can be any site adjacent to cancer cells that do not contain cancer cells.

In some aspects, the nanoparticle or first nanoparticle is a conductive nanoparticle. A conductive nanoparticle can increase conductivity and lower impedance in the cell, target site or tumor target site. Thus, in some aspects of the disclosed methods, the impedance in the cell, target site or tumor target site is lowered and/or the conductivity in the cell, target site or tumor target site is increased.

In some aspects, the second nanoparticle is a non-conductive nanoparticle. In some aspects, the non-conductive nanoparticle is not a ferroelectric nanoparticle. A non-conductive nanoparticle can decrease conductivity and increase impedance in the cell, target site or tumor target site. Thus, in some aspects of the disclosed methods, the impedance in the non-target site adjacent to the cell, target site or tumor target site is increased and/or the conductivity in the site adjacent to the cell, target site or tumor target site is decreased.

In some aspects, the current density and/or power loss density in in the cell, target site or tumor target site to the alternating current can be altered. In some aspects, the current density in the cell, target site or tumor target site is increased. In some aspects, the current density is in the cell, target site or tumor target site decreased. In some aspects, power loss density in the cell, target site or tumor target site is increased. In some aspects, power loss density in the cell, target site or tumor target site is decreased.

In some aspects, the second period of time comprises a plurality of non-contiguous intervals of time during which the second alternating electric field at the second frequency is applied to the cancer cells, wherein the plurality of non-contiguous intervals of time collectively add up to at least one week.

In some aspects, the cells are disposed in a body of a living subject, wherein the first alternating electric field is applied to the cells (e.g. tumor or cancer cells) by applying a first alternating electric field to the subject's body, the second alternating electric field is applied to the cells by applying a second alternating electric field to the subject's body, and wherein the introducing comprises administering the nanoparticle to the subject. In some aspects, the application of the first and second alternating fields occurs at a location on the subject's body based on the type and location of a cancer in the subject. For example, for glioblastoma the first and second alternating fields can be applied to the head.

In some aspects, the first alternating electric field has a field strength of at least 1 V/cm RMS. In some aspects, the first alternating electric field has a field strength between 1 and 4 V/cm RMS.

In some aspects, the disclosed methods further comprise introducing a second nanoparticle to a site adjacent to the cancer cells in the subject. In some aspects, the site can be any site adjacent to the cancer cells that do not contain cancer cells. In some aspects, the second nanoparticle is a non-conductive nanoparticle. In some aspects, the non-conductive nanoparticle is not a ferroelectric nanoparticle. A non-conductive nanoparticle can decrease conductivity and increase impedance in or at the site adjacent to the cancer cells. Thus, in some aspects of the disclosed methods, the impedance in the site adjacent to the cancer cell is increased and/or the conductivity in the site adjacent to the cancer cell is decreased.

G. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for imaging and/or treating. In some aspects, the kit can comprise one or more of the disclosed nanoparticles. The kits also can contain equipment for applying alternating electrical fields.

Disclosed herein are kits comprising one or more of the nanoparticles described herein in and a device capable of administering an alternating electric field. For example, disclosed herein are kits comprising one or more of the nanoparticles described herein in and a TTFields device (e.g Optune®, Novocure Ltd.).

EXAMPLES

Using Nanoparticals to Increase Tumor Condectivity and Enhance Alternating Electric Fields Intensity in the Tumor Preclinical studies showed a correlation between Tumor treating fields (TTFields) efficacy in killing cancer cells and field intensity [1]. A recent study [2] showed that TTFields intensity in tumor region correspond with outcome in newly diagnosed glioblastoma patients. In that study, TTFields intensity was calculated utilizing computational simulations of patient-specific head models of 317 patients treated with TTFields (at 200 kHz). The dielectric properties assigned to the models in these simulations were based on values from the literature [3-4] and the metric for TTFields intensity was defined as the minimal power density out of the two values originated from each pair of transducer arrays used to deliver TTFields to the patient head (named LMiPD).

In order to demonstrate the influence of enhanced tumor conductivity on TTFields intensity in the tumor, 45 models of patients were utilized from the computational study [2] and the electrical conductivity of the gross tumor volume was increased by 25% (0.3 S/m instead of 0.24 S/m) and the simulations were re-run. The results of these studies demonstrate that for all 45 patients, increasing tumor conductivity enhance the average LMiPD in the gross tumor volume by a similar or higher percentage than the relative increase in conductivity, as shown in FIG. 1A (26%-46%, median=32%, std=4%). Intensity increase was observed for various tumor volumes (206-85091 $mm^3$). These results indicate that increasing tumor conductivity can result in enhancement of TTFields efficacy.

A study investigating the influence of gold nanoparticles (GNP) on tissue conductivity has shown that integrating GNP enhanced tissue conductivity [6]. This study reported that at frequency of 10 kHz, the average conductivity of minced fat tissue increased from 0.0191 S/m to 0.0198 S/and from 0.55 S/m to 0.57 S/m in minced muscle tissue.

A study investigating the effect of nano-Titanium dioxide (nano-TiO2) on the signal of Electrical Impedance Tomography (EIT) showed that injecting nano-TiO2 to tumors of mice inoculated with tumors at their armpits enhanced the EIT signal [7]. This study reports that at 40 kHz the tumor impedance decreased after the injections of the nano-TiO2 particles from 12.5 kOhm to 11.2 kOhm, an increase of 12% in conductivity.

Studies investigating the conductivity of nanoparticles in solutions were also performed. A study investigating the electrical conductivity of iron oxide nanoparitlce dispersed in ethylene glycol-based fluid showed that the electrical conductivity of the nano-fluid increased from 0.39 µS/cm to 2.419 mS/cm for a loading of 4 vol % iron oxide at 25° C. [8].

Polyethylene glycol (PEG) frequently used as encapsulation agent because of non-toxic properties, and it can increase the dispersibility of nanoparticles. PEG is advantageous to prevent agglomeration and to increase penetration of the nanoparticles into the cells environment. A study investigating the dielectric properties of Mn0.5Zn0.5Fe2O4 nanoparticles (MNPs) encapsulated by PEG report that MNPs remain conducting after encapsulating at frequency range 5 kHz to 120 kHz. [9]

REFERENCES

[1] Kirson, E. D., Dbalý, V., Tovarys, F., Vymazal, J., Soustiel, J. F., Itzhaki, A., Mordechovich, D., Steinberg-Shapira, S., Gurvich, Z., Schneiderman, R., Wasserman, Y., Salzberg, M., Ryffel, B., Goldsher, D., Dekel, E., Palti, Y. (2007). Alternating electric fields arrest cell proliferation in animal tumor models and human brain tumors. Proceedings of the National Academy of Sciences of the United States of America, 104(24), 10152-7.

[2] M Ballo, Z Bomzon, N Urman, G Lavy-Shahaf, S A Toms; P01.113 Increasing TTFields dose to the tumor bed improves overall survival in newly diagnosed glioblastoma patients, *Neuro-Oncology*, Volume 20, Issue suppl_3, 19 Sep. 2018, Pages iii257, https://doi.org/10.1093/neuonc/noy139.155

[3] N Urman, S Levy, A Frenkel, A Navch, H S Hershkovich, E Kirson, C Wenger, G Lavy-Shahaf, D Manzur, O Yesharim, Z Bomzon; P04.57 Creating patient-specific computational head models for the study of tissue-electric field interactions using deformable templates, *Neuro-Oncology*, Volume 20, Issue suppl_3, 19 Sep. 2018, Pages iii292, https://doi.org/10.1093/neuonc/noy139.291

[4] Wenger C, Salvador R, Basser P J, Miranda P C. The electric field distribution in the brain during TTFields therapy and its dependence on tissue dielectric properties and anatomy: a computational study. Phys Med Biol. 2015; 60(18):7339-57.

[5] Hershkovich H S, Bomzon Z, Wenger C, Urman N, Chaudhry A, Garcia-Carracedo D, Kirson E D, Weinberg U, Wassermann Y, Palti Y., "First steps to creating a platform for high throughput simulation of TTFields", Conf Proc IEEE Eng Med Biol Soc. 2016 August; 2016: 2357-2360. doi: 10.1109/EMBC.2016.7591203.

[6] Ostovari M, Riahi Alam, Zabihzadch, Gharibvand, Hoscini-Ghahfarokhi; "The Effect of Gold Nanoparticles on Electrical Impedance of Tissue on Low Frequency Ranges", J Biomed Phys Eng. 2018 Sep. 1; 8(3):241-250. eCollection 2018 September.

[7] Liu R1, Jin C, Song F, Liu J. "Nanoparticle-enhanced electrical impedance detection and its potential significance in image tomography", Int J Nanomedicine. 2013; 8:33-8. doi: 10.2147/IJN.S37275. Epub 2013 Jan. 3.

[8] Jamilpanah, P., Pahlavanzadch, H. & Kheradmand, A. "Thermal conductivity, viscosity, and electrical conductivity of iron oxide with a cloud fractal structure", Heat Mass Transfer (2017) 53: 1343. https://doi.org/10.1007/s00231-016-1891-5

[9] L. Armitasari et al. "Effect of Polyethylene Glycol (PEG-4000) on Dielectric Properties of Mn0.5Zn0.5Fe2O4 Nanoparticles", 2018 *IOP Conf. Ser.: Mater. Sci. Eng.* 367 012035.

Barium Titanate Nanoparticles Sensitize Treatment-Resistant Breast Cancer Cells to the Antitumor Action of Tumor-Treating Fields Introduction: Many preclinical and clinical studies indicate that TTFields would be applicable for other tumor types including breast, lung, pancreatic, and ovarian cancers. Early clinical trials have shown that only TTFields treatment for GBM patients was not significantly better than conventional chemotherapy. However, recent preclinical studies suggest that combination therapy of TTFields with conventional treatments including chemotherapy, immunotherapy, and radiotherapy are more effective than TTFields monotherapy in GBM. Despite the promise shown by TTFields as a viable cancer therapy, not much is known about TTFields responsive sensitiser.

Ferroelectric nanomaterials (non-conductive nanoparticles) have emerged as promising tools for enhancing electric stimulation of cells and tissues. Among ferroelectric materials, barium titanate nanoparticles (BTNPs) have high dielectric constants and suitable piezoelectric characteristics with high biocompatibility. Recent reports suggest that BTNPs could be used in a wide range of applications in nanomedicine, including non-linear imaging purposes, drug delivery, tissue engineering, and bio-stimulation. For instance, BTNPs promote higher internalisation of doxorubicin in human neuroblastoma cells and BTNPs with polyethylenimine have been shown to improve cellular uptake for cell imaging and DNA delivery. Disclosed herein are studies that investigated whether BTNPs could enhance the antitumor action of TTFields in response to TTFields. The data herein shows that BTNPs alone are cytocompatible with breast cancer cells, but in response to TTFields, it can sensitize TTField-resistant breast cancer cells to the antitumor action of TTFields. Further, the data herein demonstrates that BTNPs were taken up by TTFields stimulation and these promoted antitumor action of TTFields by enhancing cell cycle-related apoptosis in breast cancer cells. Therefore, this study shows a TTField-responsive sensitiser, BTNPs, in breast cancer cells. The studies described herein can be performed on other cancer cells to show additional evidence that BTNPs may be taken up by TTFields stimulation and these promoted antitumor action of TTFields by enhancing cell cycle-related apoptosis in other cancer cell types.

Results

Characteristics and Cytocompatibility of BTNPs in Breast Cancer Cells

Figures 3A, 3B, 3C:
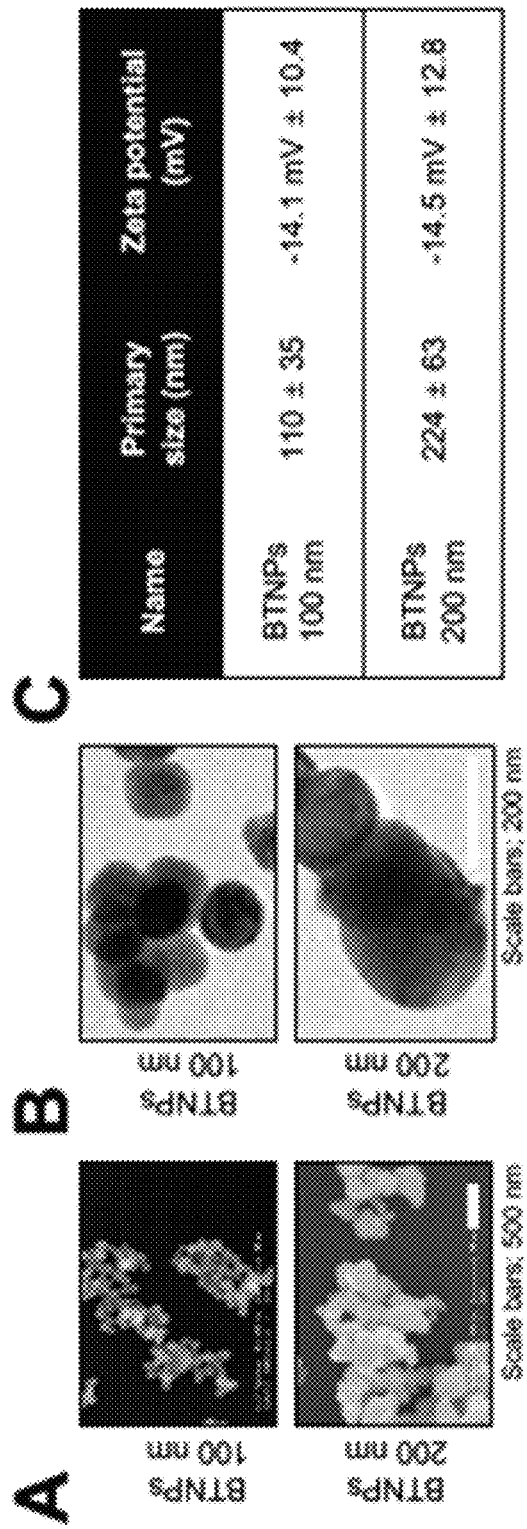
FIG. 3A, FIG. 3B, and FIG. 3C show physicochemical characterization of BTNPs.
Figures 4A, 4B, 4C, 4D, 4E, 4F:
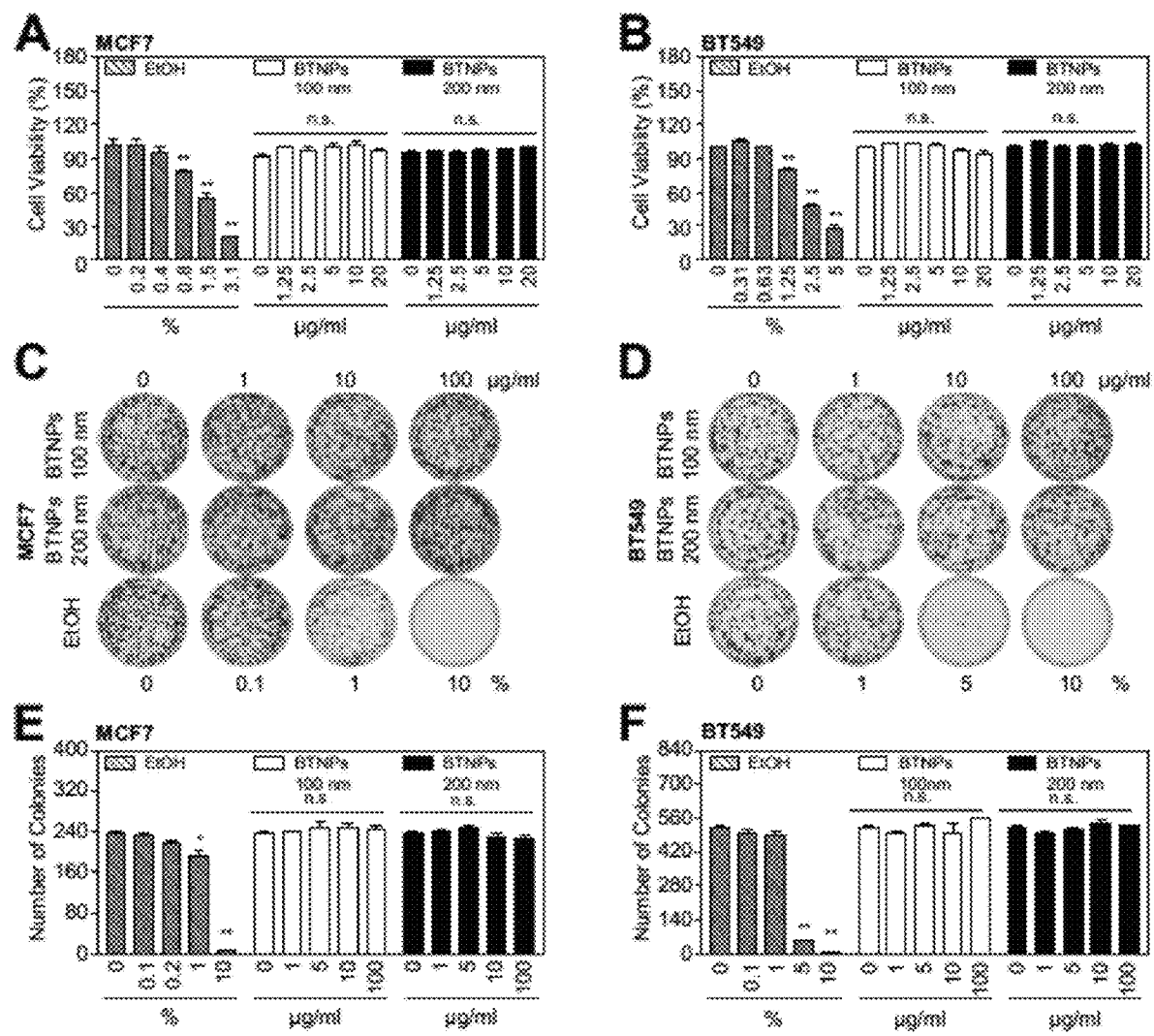
FIG. 4A, FIG. 4B, FIG. 4C, FIG. 4D, FIG. 4E, and FIG. 4F show cytocompatibility of BTNPs in breast cancer cells.

Since dielectric permittivity of BTNPs can be maximized depending on its size, two different sizes of FBS (fetal bovine serum) coated BTNPs were prepared (100 nm and 200 nm). The SEM images of 100 nm and 200 nm BTNPs showed typical round shape and homogeneous size of the nanoparticles (FIGS. 3A and 3B). The hydrodynamic radius of 100 nm and 200 nm BTNPs were 110±35 nm and 224±63 nm and the Zeta potentials of 100 nm and 200 nm BTNPs were −14.1±10.4 mV and −14.5±12.8 mV, respectively (FIG. 3C), indicating that BTNPs were relatively stable in aqueous dispersions. Next, the cytocompatibility of 100 nm and 200 nm BTNPs were examined by cell viability and clonogenic assay in the two breast cancer cell lines, MCF-7 and BT-549. Ethanol was used as a positive control in these assays. The cell viability assay indicated that treatment with 100 nm and 200 nm BTNPs up to a concentration of 20 μg/ml did not affect cell viability in MCF-7 and BT-549 cells (FIG. 4A and FIG. 4B). In addition, the clonogenic assay showed that treatment with 100 nm and 200 nm BTNPs up to a concentration of 100 μg/ml did not affect colony formation in MCF-7 and BT-549 cells (FIGS. 4C-F). Taken together, these results indicate that BTNPs exhibit cytocompatibility with non-cytotoxic effects in breast cancer cells.

BTNPs Sensitise TTField-Resistant Breast Cancer Cells in Response to TTFields

Figures 5A, 5B, 5C:
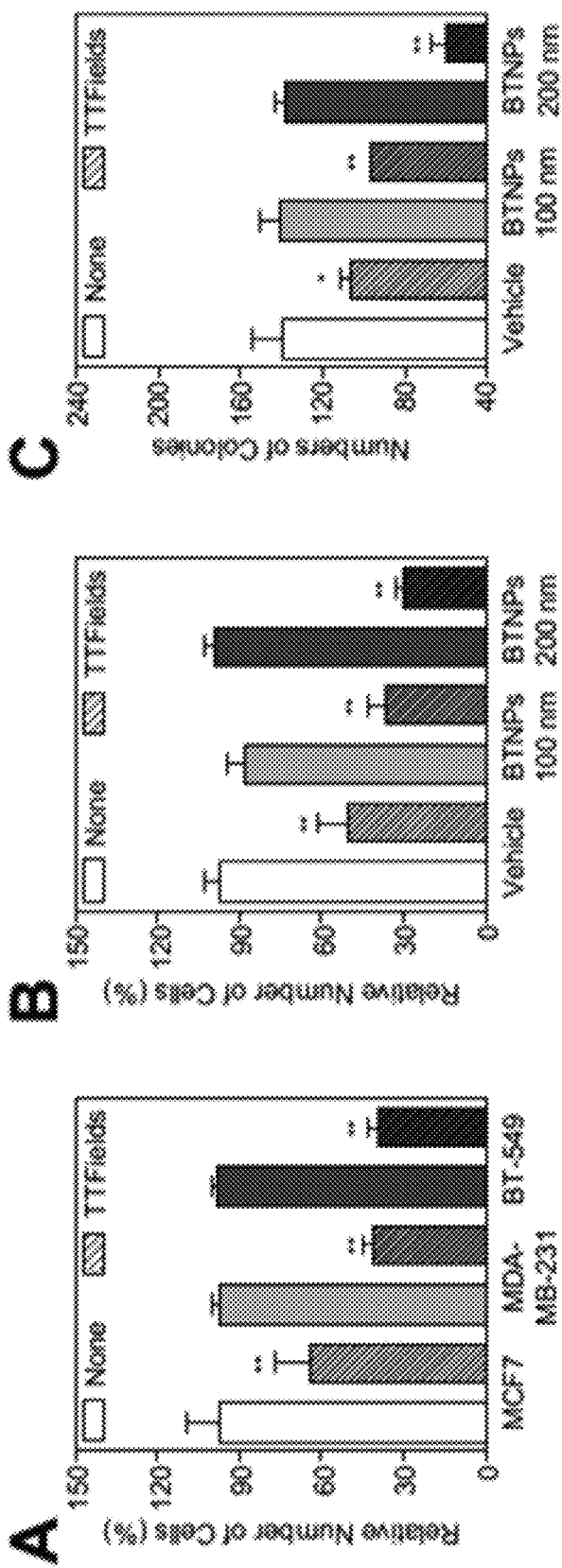
FIG. 5A, FIG. 5B, and FIG. 5C show BTNPs enhanced the antitumor activity of TTFields in low TTField-sensitive MCF-7 cells.

TTFields efficacy was tested in three breast cancer cell lines, MCF-7, MDA-MB-231, and BT-549. Among these, MCF-7 cells were the most resistant to TTFields (FIG. 5A), which is consistent with previous reports. Thus, the combinatorial effect of BTNPs and TTFields was examined in MCF-7 cells. Cell viability and clonogenic assays showed that treatment with 100 nm and 200 nm BTNPs enhanced the antitumor action of TTFields in TTField-resistant MCF-7 cells (FIGS. 5B-D). Notably, 200 nm BTNPs were more potent than the 100 nm ones (FIGS. 5B-D), indicating that size can be an important factor in the antitumor activity of BTNPs in presence of TTFields. Thus, these results indicated that BTNPs sensitize TTField-resistant breast cancer cells in response to TTFields.

TTFields Induce the Cytosolic Accumulation of BTNPs in Breast Cancer Cells

Figures 6A, 6B, 6C, 6D, 6E:
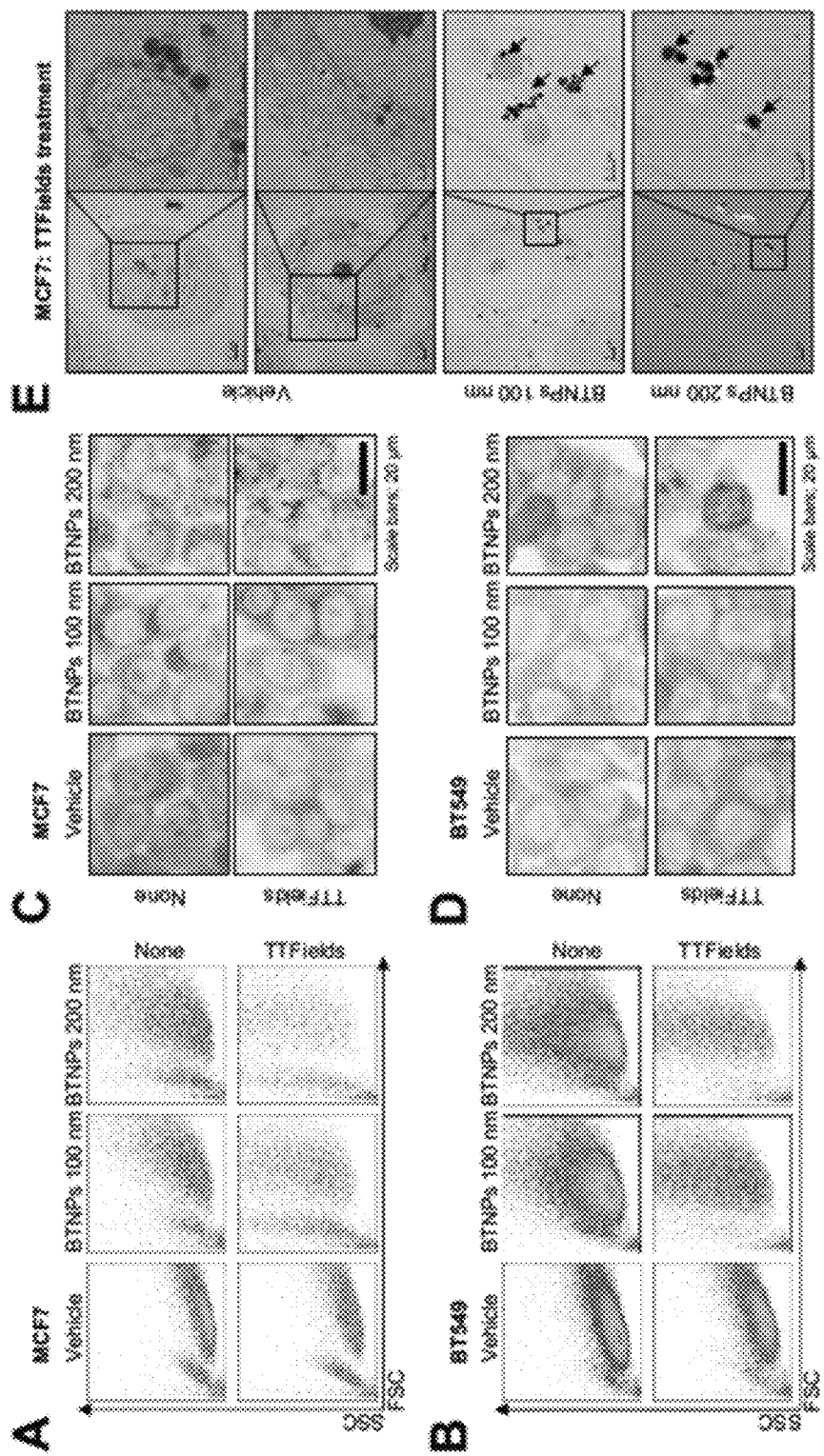
FIG. 6A, FIG. 6B, FIG. 6C, FIG. 6D, and FIG. 6E show cytoplasmic accumulation of BTNPs in MCF-7 and BT-549 cells in response to TTFields.

To investigate the mechanism of this sensitization mediated by BTNPs in presence of TTFields, whether BTNPs accumulate into breast cancer cells in response to TTFields was examined. First, a fluorescence-activated cell sorting (FACS) analysis was performed to determine cell size and granularity in TTField-treated and BTNP/TTField-treated cells. These parameters were similar between the control and TTField-treated MCF-7 and BT-549 cells (FIG. 6A and FIG. 6B, left panels). Cell size and granularity increased in BTNP/TTField-treated MCF-7 and BT-549 cells (FIG. 6A and FIG. 6B, middle and right panels). In addition, methylene blue staining showed the cytosolic accumulation of BTNPs in response to TTFields in MCF-7 and BT-549 cells (FIG. 6C and FIG. 6D). In addition, transmission electron microscopy (TEM) analysis showed that BTNPs accumulated in the cytoplasm of in TTField-treated MCF cells (FIG. 6E). Therefore, these results indicated that BTNPs accumulated into the cytoplasm of breast cancer cells in response to TTFields.

TTFields Combined with BTNPs Modulates Cell Cycle-Apoptosis Pathways

Figures 7A, 7B:
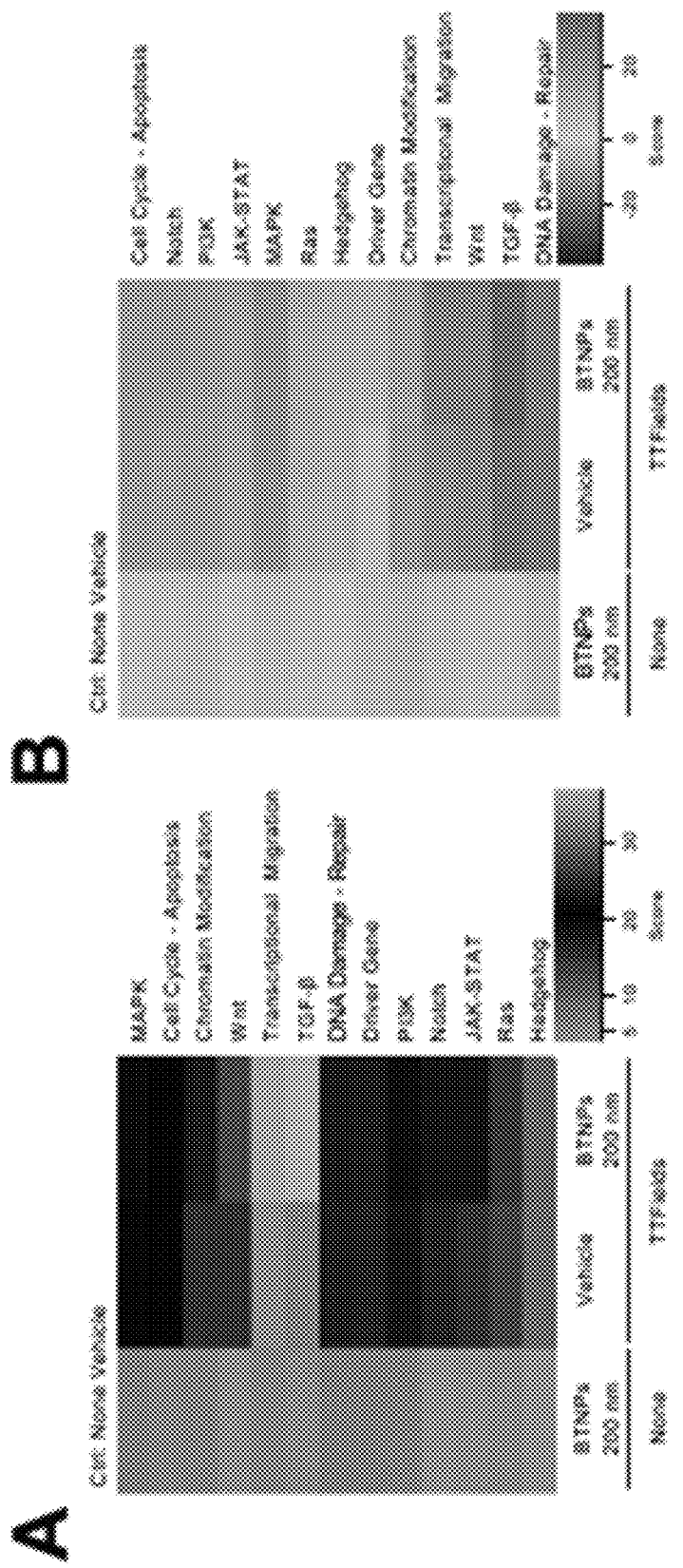
FIG. 7A and FIG. 7B show changes in gene copy number in MCF-7 cells on TTFields and BTNP combinatorial treatment.
Figures 8A, 8B:
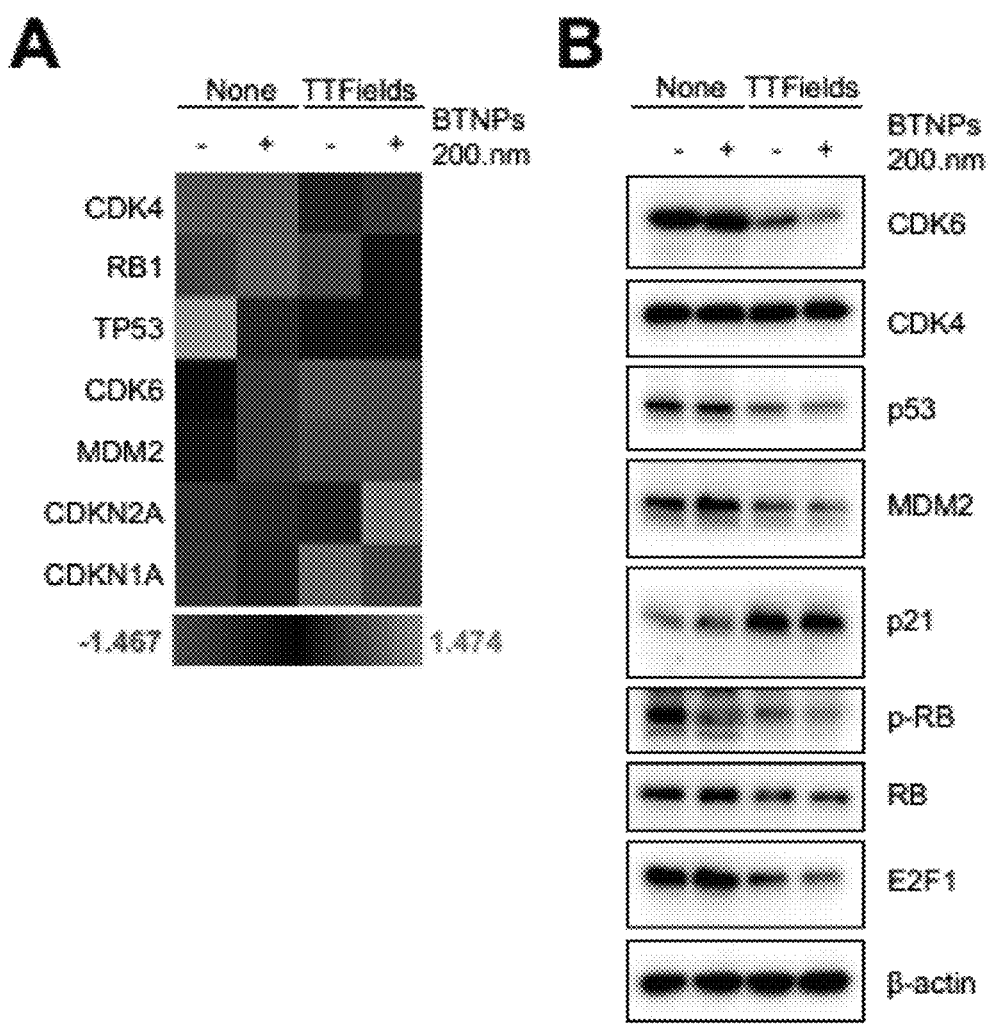
FIG. 8A and FIG. 8B show modulation of cell cycle-apoptosis pathways by BTNPs combined with TTFields.

To further investigate the regulatory action of the TTFields/BTNPs combination approach, a NanoString nCounter™ Pan-Cancer pathway analysis containing probes targeting 700 transcripts related to 13 types of cancer pathways was carried out in MCF-7 cells exposed to TTFields and treated without or with 200 nm BTNPs for 48 hrs. MCF-7 cells treated with BTNPs with no exposure to TTFields was also included as a control. The gene expression patterns were similar between control and BTNPs-treated MCF-7 cells, while TTFields treatment induced dramatic changes in 9 different types of cancer pathways (FIG. 7A). Among them, cell cycle-apoptosis, Wnt, transcriptional migration, transforming growth factor beta (TGF-β), driver gene, Notch, Janus kinase-signal transducer and activator of transcription (JAK-STAT), and Ras signalling were significantly modulated in TTField-treated and BTNP/TTField-treated MCF-7 cells (FIG. 7B), evidencing that BTNPs/TTFields can have a capacity to modulate several cancer signaling pathways. Cell cycle pathways were further analyzed. The data showed that several cell cycle regulatory transcripts including cyclin dependent kinase 4 (CDK4), RB1, tumor protein TP53, cyclin dependent kinase 6 (CDK6), MDM2, and CDKN1A/2A were modulated in BTNP/TTField-treated MCF-7 cells (FIG. 8A). In addition, Western blot analysis for the cell cycle regulatory genes also showed that TTFields combined with BTNPs inhibited cell cycle progression, as determined by significant decreases in CDK6 and transcription factor E2F1 (FIG. 8B). These results indicate that TTFields combined with BTNPs exerts anticancer activity on breast cancer cells by modulating cancer-related pathways, and specifically inhibiting cell cycle progression.

Discussion

BTNPs had non-cytotoxic effects in breast cancer cells and enhanced the antitumor activity of TTField-resistant breast cancer cells in response to TTFields. Further, it was found that TTFields triggered the accumulation of BTNPs, which promoted the cell cycle-related apoptosis pathway. These data show that biocompatible nanomaterials such as BTNPs can be used as a TTField-responsive sensitizer in cancer cells.

These results showed that BTNPs had non-cytotoxic effects even at high concentrations (100 μg/ml) in breast cancer cells, indicating that these are biocompatible. Consistent with these results, other reports have shown that treatment with BTNPs have minimal adverse effects, as evident from several assays including metabolic activity, viability/cytotoxicity, early apoptosis, and reactive oxygen species (ROS) generation in multiple types of cells such as human neuroblastoma SH-SY5Y cells, HeLa cells, and rat mesenchymal stem cells. The results also show that treatment with only BTNPs did not significantly alter the 13 types of major cancer pathways and cell cycle regulatory proteins (FIG. 7). BTNPs and its coated composites could be used as a biocompatible sensitizer for TTFields.

The data shows that TTFields efficacy is dependent on cell doubling time in various cancer cell lines. However, MCF-7 cells were more resistant to TTFields than MDA-MB-231 and BT-549 cells, despite the similar cell doubling time between MCF-7 and MDA-MB-231 cells. The data shows that BTNPs sensitized the TTField-resistant MCF-7 breast cancer cells in response to TTFields, indicating that the TTField-responsive sensitizers such as BTNPs could enhance the efficacy of TTFields in TTField-resistant cancer cells. In this context, several studies showed that chemotherapeutic agents or radiotherapy enhance the efficacy of TTFields in various cancer cells. However, these combination treatments do not respond to TTFields, indicating that conventional chemotherapeutic agents or radiotherapy is not a specific sensitizer for TTFields, which is a physical treatment modality. Therefore, the data indicates that BTNPs can be used as a TTField-responsive sensitiser for TTField-resistant tumors.

The data shows that BTNPs were accumulated into the cytoplasm of breast cancer cells in response to TTFields. Nanoparticles (NPs) internalization into cells is known to be dependent on particle size and its zeta potential. NPs under 200 nm can be engulfed by cancer cells through clathrin-dependent pathway or macro-pinocytosis pathway. However, specific inhibitors for these pathways, such as chlorpromazine, amiloride, and cytochalasin D, did not modulate the accumulation of BTNPs in cytoplasm in response to TTFields, indicating that BTNP accumulation in cytoplasm is not mediated by clathrin-dependent pathway or macro-pinocytosis pathway. The data herein evidences that increased membrane permeability by TTFields can induce BTNP accumulation in cytoplasm of cancer cells.

Figure 9:
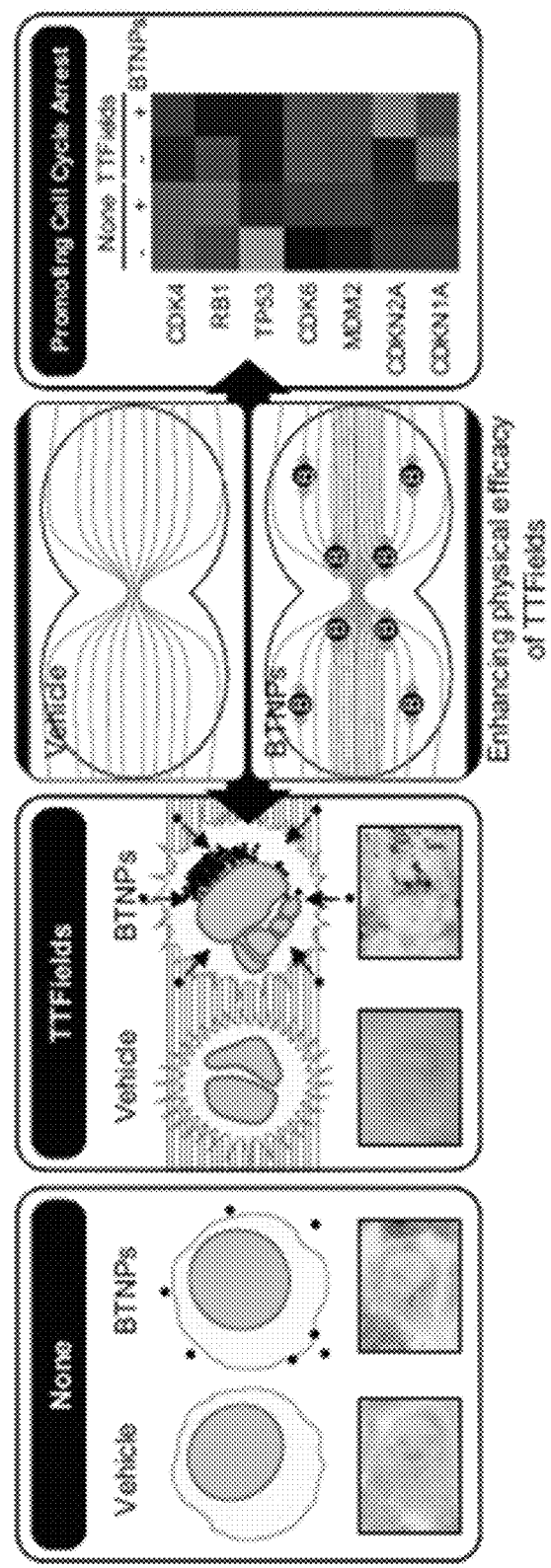
FIG. 9 shows a schematic representation of the proposed mechanism of cancer cell sensitization induced by BTNPs in presence of TTFields.

The data herein indicates that TTFields combined with BTNPs significantly modulated the cell cycle-apoptosis pathways over other related pathways. Since cells with mitotic defects undergo mitotic catastrophe or G1-arrest senescence, the data shows that TTFields combined with BTNPs could induce mitotic catastrophe and G1-arrest senescence by modulating cell cycle-apoptosis pathway, as evident by the decrease in G1 cell cycle regulators including CDK4/6, p-RB, and E2F1 in the BTNPs/TTField-treated cells. In addition to cell cycle-apoptosis pathway, significant modulation of several cancer pathways including Wnt, transcriptional migration, transforming growth factor beta (TGF-β), driver gene, Notch, Janus kinase-signal transducer and activator of transcription (JAK-STAT), and Ras signalling were observed in TTField-treated and BTNPs/TTField-treated MCF-7 cells. The data also shows that BTNPs, characterized by their high biocompatibility and ferroelectric properties, acts as a TTField-responsive sensitizer to breast cancer cells by modulating cell cycle-apoptosis pathway (FIG. 9). Therefore, electric field responsive nanomaterials, such as BTNPs, can be used as a TTField-responsive sensitizer to enhance the therapeutic efficacy of TTFields in cancer cells.

Methods

Cell culture: MCF-7 and BT-549 breast cancer cell lines were purchased from American Type Culture Collection (ATCC, Manassas, VA). As confirmed by the information provided by ATCC, both cell lines were authenticated by their karyotypes, images, and detailed gene expression. Both cell lines were preserved and passaged in less than 2 months in accordance with ATCC protocols, and tested for mycoplasma infection by polymerase chain reaction (PCR) once a week. MCF-7 cells were cultured in Dulbecco's Modified Eagle Media (DMEM, Corning, NY, USA) and BT-549 cells were cultured in RPMI (Corning, NY, USA). All media types were supplemented with 10% fetal bovine serum (FBS, Corning, NY, USA) and 1% penicillin/streptomycin (Sigma-Aldrich, MO, USA). All cell lines were maintained in a humidified 5% CO2 incubator at 37° C.

TTFields application: MCF-7 ($1.5 \times 10^4$) and BT-549 ($1 \times 10^4$) cells were seeded on 18 mm glass coverslips (Marienfeld-Superior, Mediline, Lauda-Königshofen, Germany) or 22 mm plastic coverslips (Thermo Fisher Scientific, MA, USA) for 24 hrs and those coverslips were transferred to ceramic inovitro dishes (NovoCure, Haifa, Israel) using autoclaved forceps. For TTFields treatment, we applied the inovitro system (NovoCure, Haifa, Israel) for 72 hrs as described previously. Briefly, cells on a coverslip were exposed to 1 V/cm at 150 kHz with a current of 150 mA generated by inovitro TTFields generators (NovoCure, Haifa, Israel) and the plate temperature was maintained at 37° C. by a refrigerated incubator (ESCO Technologies, USA) at 19° C.

Generation and physicochemical characterization of BTNPs: Barium titanate nanoparticles (100 nm, 200 nm) were purchased from US Research Nanomaterials Inc. (TX, USA) and used without further purification. BTNPs were dispersed in ethanol and sonicated to mitigate aggregation. In addition, 5% FBS was added to coat the surface of BTNPs with a protein corona, before addition to cells. The nanostructures and morphologies of prepared BTNPs were examined by field emission scanning electron microscopy (FE-SEM) with a Sirion-400 (FEI, OR, USA) and TEM with a JEM-2100F (JEOL, Japan). The zeta-potential of FBS coated BTNPs were measured by dynamic light scattering in a Zetasizer Nano ZS (Malvern Instruments Ltd., UK).

Cell viability assay: Cell viability assays were performed using WST-8 reagent (Cyto X; LPS solution, Daejeon). MCF-7 cells ($0.5 \times 10^4$) were seeded on a 96-well plate and treated with media containing increasing concentrations of BTNPs or ethanol as a vehicle control. After 72 hrs, WST-8 reagent (10 μl) was added to each well and the plate incubated for 2 hrs at 37° C. Subsequently, the absorbance was measured at 450 nm using a VersaMax Microplate Reader (Molecular Devices, CA, USA).

Clonogenic assay: The clonogenic assay was performed as described previously. MCF-7 or BT-549 cells (500 in number) were seeded on a 22 mm plastic coverslip in a 6-well plate for 24 hrs. Using autoclaved forceps, the coverslips were transferred to ceramic inovitro dishes and incubated with inovitro TTFields generators for 72 hrs. After TTFields treatment, the coverslips were transferred to a 6-well plate and incubated at 37° C. After 7 days, colonies were fixed and stained with 1% crystal violet (Sigma-Aldrich) and 40% methanol solution, and the number of colonies counted.

Cell counting: To evaluate the number of alive cells in the same volume, absolute cell counts were acquired using a BD Accuri™ C6 flow cytometer (BD Biosciences, CA, USA) as described previously. Briefly, detached MCF-7 and BT-549 cells in fresh media (500 μl) were stained with propidium iodide (50 μg/ml; PI; Sigma-Aldrich, MO, USA) and the number of cells in PI-negative population was counted in a 100 μl volume.

Cell cycle analysis: Cell cycle analysis was performed. Briefly, the cells treated with conditions described above were trypsinised, washed twice in PBS, and fixed with ice-cold 70% ethanol. Fixed cells were incubated with PI (50 μg/ml) and RNase (100 μg/ml) at 37° C. for 30 min and then analyzed with a BD Accuri™ C6 flow cytometer (BD Biosciences, CA, USA).

Apoptosis analysis: Detached cells were collected and apoptosis detected using the FITC Annexin V Apoptosis Detection Kit (BD Biosciences, CA, USA) following the manufacturer's protocol. The samples were analyzed using a BD Accuri™ C6 flow cytometer (BD Biosciences, CA, USA).

Methylene blue staining: Cells were fixed with 4% paraformaldehyde, and then stained with 0.1% methylene blue (Sigma-Aldrich, MO, USA) dissolved in Dulbecco's phosphate-buffered saline (DPBS) for 5 min. After washing several times with DPBS, the slides were mounted in glycerol and images obtained using an LSM 710 confocal microscope (Carl Zeiss Inc., Germany).

TEM imaging: TTFields treated MCF-7 cells with and without BTNP treatment were detached and fixed in 2.5% glutaraldehyde (Sigma-Aldrich, MO, USA) and 0.1 M phosphate buffer (pH 7.3) at 4° C. overnight. After this fixation, the cells were treated with 1% osmium tetroxide and 1.5% potassium ferrocyanide in 0.1 M phosphate buffer (pH 7.3) for 1 h at 4° C. in dark. Subsequently, these were embedded in Epon 812 (Sigma-Aldrich, MO, USA) after dehydration in a treatment cycle of ethanol and propylene oxide. The polymer reaction was carried out by using pure resin at 70° C. for two days. Ultrathin samples were obtained with an UltraCut-UCT ultramicrotome (Leica, Austria) and collected on 150 mesh copper grids. After staining with 2% uranyl acetate for 10 min and lead citrate for 5 min, the samples were examined at 120 kV in a Tecnai G2 Spirit Twin TEM setup.

RNA isolation and NanoString analysis: Total RNA was isolated using QIAzol reagents (Qiagen, Hilden, Germany) from treated cells. Following the procedures provided by the nCounter XT CodeSet Gene Expression Assays (NanoString Technologies, WA, USA), 100 ng of RNA was used to hybridize with probes.

Western blot analysis: Western blotting was performed as described previously. Briefly, proteins were separated by SDS-polyacrylamide gel electrophoresis, transferred to a nitrocellulose membrane, and detected using specific antibodies. The following antibodies were used: rabbit polyclonal anti-CDK4, rabbit monoclonal CDK6, rabbit monoclonal phospho-RB, rabbit polyclonal RB (Santa Cruz Biotechnology, CA, USA); mouse monoclonal p21, mouse monoclonal E2F1, mouse monoclonal MDM2, mouse polyclonal anti-β-actin (Santa Cruz Biotechnology, CA, USA), and mouse monoclonal p53 (Merck, NJ, USA). Blots were developed using peroxide-conjugated secondary antibody and visualized with an enhanced chemiluminescence detection system (Amersham Life Science, Buckinghamshire, UK).

Statistical analysis: The two-tailed Student's t-test was performed to analyze statistical differences between groups. P-values of less than 0.05 were considered statistically significant. Statistical analyses were performed using Microsoft Excel and XLSTAT software.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of increasing the efficacy of an alternating electric field in a tumor target site of a subject, the method comprising:
   a. introducing a conductive nanoparticle to a tumor target site in the subject;
   b. applying an alternating electric field to the tumor target site, wherein the tumor target site is adjacent to one or more cancer cells, wherein the alternating electric field has a frequency of 50 to 400 kHz, wherein the efficacy of the alternating electric field in the tumor target site of the subject is increased, wherein the increased efficacy of the alternating electric field in the tumor target site results in an increased anti-mitotic effect of the alternating electric field in the tumor target site.

2. The method of claim 1, wherein the alternating electric field has a current density, wherein a magnitude of the current density of the alternating electric field is increased in the tumor target site.

3. The method of claim 1, wherein the tumor target site has a lowered electric impedance.

4. The method of claim 1, wherein the tumor target site has an increased conductivity.

5. The method of claim 1, wherein the impedance in the site adjacent to the tumor target site is increased.

6. The method of claim 1, wherein the alternating electric field is a tumor-treating field.

7. The method of claim 1, further comprising introducing a non-conductive nanoparticle to a site adjacent to the tumor target site in the subject.

8. The method of claim 7, wherein the tumor target site has an increased electric impedance.

9. The method of claim 7, wherein the tumor target site has a lowered conductivity.

10. The method of claim 7, wherein the non-conducting nanoparticle is not a ferroelectric nanoparticle.

11. The method of claim 7, wherein the site adjacent to the tumor target site has an increased electric impedance.

12. The method of claim 7, wherein the site adjacent to the tumor target site has a lowered conductivity.

13. The method of claim 7, wherein the nanoparticles are nanoparticles that increase tissue permittivity.

* * * * *